United States Patent [19]

Reiffenrath et al.

[11] Patent Number: 5,279,764

[45] Date of Patent: Jan. 18, 1994

[54] DIHALOGENOBENZENE DERIVATIVES

[75] Inventors: Volker Reiffenrath, Rossdorf; Joachim Krause, Dieburg; Georg Weber, Erzhausen; Ulrich Finkenzeller, Plankstadt; Andreas Wächtler, Griesheim; Thomas Geelhaar, Mainz, all of Fed. Rep. of Germany; David Coates, Merley, Great Britain; Ian C. Sage, Broadstone, Great Britain; Simon Greenfield, Creekmor, Great Britain

[73] Assignee: Merck Patent Gesellschaft mit beschränkter Haftung, Darmstadt, Fed. Rep. of Germany

[21] Appl. No.: 980,140

[22] Filed: Nov. 23, 1992

Related U.S. Application Data

[63] Continuation of Ser. No. 321,426, Mar. 9, 1989, abandoned.

[30] Foreign Application Priority Data

Mar. 10, 1988 [DE] Fed. Rep. of Germany ....... 3807908

[51] Int. Cl.$^5$ ............... C09K 19/12; C07C 41/00; C07C 69/76; C07C 255/00; C07C 19/08
[52] U.S. Cl. ................ 252/299.66; 558/388; 558/389; 558/396; 558/398; 558/399; 558/401; 558/411; 558/414; 558/415; 558/416; 558/425; 560/59; 560/65; 560/129; 560/130; 560/147; 560/179; 560/184; 560/188; 568/74; 568/645; 568/647; 568/655; 568/663; 570/127; 570/128
[58] Field of Search ........... 252/299.01, 299.6, 299.66; 568/645, 647, 655, 663, 74; 558/388, 389, 396, 398, 399, 401, 411, 414, 415, 416, 425; 560/59, 65, 129, 130, 147, 179, 184, 188; 570/127, 128

[56] References Cited

U.S. PATENT DOCUMENTS

| | | | |
|---|---|---|---|
| 4,009,934 | 3/1977 | Goodwin et al. | 252/299.01 |
| 4,368,135 | 1/1983 | Osman | 252/299.63 |
| 4,415,470 | 11/1983 | Eidenschink et al. | 252/299.63 |
| 4,419,264 | 12/1983 | Eidenshink et al. | 252/299.63 |
| 4,514,317 | 4/1985 | Tuong et al. | 252/299.62 |
| 4,545,922 | 10/1985 | Eidenshink et al. | 252/299.63 |
| 4,551,264 | 11/1985 | Eidenschink et al. | 252/299.63 |
| 4,602,851 | 7/1986 | Jenner et al. | 252/299.67 |
| 4,606,845 | 8/1986 | Romer et al. | 252/299.63 |
| 4,630,897 | 12/1986 | Andrews et al. | 252/299.61 |
| 4,637,897 | 1/1987 | Kelly | 252/299.63 |
| 4,659,502 | 4/1987 | Fearon et al. | 252/299.63 |
| 4,664,840 | 5/1987 | Osman | 252/299.63 |
| 4,696,759 | 9/1987 | Isoyama et al. | 252/299.63 |
| 4,704,227 | 11/1987 | Krause et al. | 252/299.61 |
| 4,710,315 | 12/1987 | Schad et al. | 252/299.63 |
| 4,724,097 | 2/1988 | Romer et al. | 252/299.63 |
| 4,744,918 | 5/1988 | Heppke et al. | 252/299.01 |
| 4,776,973 | 10/1988 | Bofinger et al. | 252/299.61 |
| 4,808,333 | 2/1989 | Huynh-Ba et al. | 252/299.61 |
| 4,820,839 | 4/1989 | Krause et al. | 252/299.61 |
| 4,834,904 | 5/1989 | Krause et al. | 252/299.61 |
| 4,834,904 | 5/1989 | Krause et al. | 252/299.61 |
| 4,897,216 | 1/1990 | Reffenrath et al. | 252/299.63 |
| 4,925,278 | 5/1990 | Buchecker et al. | 252/299.01 |
| 4,925,590 | 5/1990 | Reiffenrath et al. | 252/299.61 |
| 5,087,764 | 2/1992 | Reiffenrath et al. | 568/656 |

FOREIGN PATENT DOCUMENTS

| | | |
|---|---|---|
| 0051738 | 3/1981 | European Pat. Off. . |
| 0133489 | 7/1984 | European Pat. Off. . |
| 2939782 | 4/1981 | Fed. Rep. of Germany ................... 252/299.64 |
| 2098986 | 12/1982 | United Kingdom ........... 252/299.67 |
| 8802130 | 3/1988 | World Int. Prop. O. ...... 252/299.01 |

OTHER PUBLICATIONS

Osman, M. A. et al., Mol. Cryst. Liq. Crys., vol. 42 (Lett.), pp. 57–62 (1983).

Primary Examiner—Philip Tucker
Attorney, Agent, or Firm—Millen, White, Zelano & Branigan

[57]  ABSTRACT

The invention relates to dihalogenobenzene derivatives of the formula I $$R^1-A^1-Z^1-A^2-(Z^2-A^3)_n-R^2$$

wherein $R^1$, $R^2$, $A^1$, $A^2$, $A^3$, $Z^1$, $Z^2$ and n are as defined in the specification.

11 Claims, No Drawings

DIHALOGENOBENZENE DERIVATIVES

CROSS-REFERENCE TO RELATED APPLICATIONS

This application is a continuation of application Ser. No. 07/321,426, filed Mar. 9, 1989 now abandoned.

This application is related to commonly assigned applications of even date Ser. No. 07/321,428 now abandoned; Ser. No. 07/321,045 now U.S. Pat. No. 4,925,590; and Ser. No. 07/321,427 now abandoned, each of which disclosure is entirely incorporated by reference herein.

SUMMARY OF THE INVENTION

The invention relates to dihalogenobenzene derivatives of the formula I

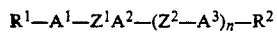

$$R^1-A^1-Z^1A^2-(Z^2-A^3)_n-R^2 \quad \text{I}$$

wherein $R^1$ and $R^2$ in each case independently of one another are a straight-chain or branched alkyl or perfluoroalkyl group having in each case 1-15 C atoms, it also being possible for one or more $CH_2$ or $CF_2$ groups to be replaced by a grouping chosen from the group comprising —O—, —S—, —CO—, —O—CO—, —S—CO, —O—COO—, —CO—S—, —CO—O—, —E—, —CH— halogeno- and —CHCN—, two hetero atoms not being linked directly, and one of the radicals $R^1$ and $R^2$ is also H, F, Cl, Br, CN, COOH, OH, SH, $NH_2$, $NO_2$, —NCS, NC or $SF_5$, is $CR^3=CR^4$,

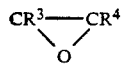

or C≡C, $R^3$ and $R^4$ in each case independently of one another are H, alkyl having 1-6 C atoms, F, Cl, Br, $CF_3$ or CN, $Z^1$ and $Z^2$ in each case independently of one another —CO—O—, —O—CO—, —CH$_2$CH$_2$—, —CH$_2$—O—, —O—CH$_2$—, N=CH$_2$—, —CH$_2$=N—, —CH$_2$—CO—, —CO—CH$_2$—, —N=N—, —NO=N—, —C≡C— or a single bond, $A^1$, $A^2$ and $A^3$ in each case independently of one another are a 1,4-phenylene group which is unsubstituted or substituted by one or more halogen, nitrile and/or alkyl substituents, it also being possible for one or more CH groups to be replaced by N, a 1,4-cyclohexylene group, it also being possible for one or two non-adjacent $CH_2$ groups to be replaced by O and/or S, or a 1,4-cyclohexenylene group, 1,4-bicyclo(2,2,2)octylene group, piperidine-1,4-diyl group, naphthalene-2,6-diyl group, decahydronaphthalene-2,6-diyl group or 1,2,3,4-tetrahydronaphthalene-2,6-diyl group and n is 0, 1, 2 or 3, with the provisos that a) at least one of the rings $A^1$, $A^2$ and $A^3$ is 2,3-dihalogeno-1,4-phenylene and b) if one of the rings $A^1$, $A^2$ and $A^3$ is a 2,3-dichloro-1,4-phenylene group, $Z^1$ and $Z^2$ in each case independently of one another are only —CH$_2$CH$_2$—, —CH$_2$O—, —O—CH$_2$—, —N=CH$_2$—, —CH$_2$=N—, —CH$_2$—CO—, —CO—CH$_2$—, —N=N—, —NO=N—, —N=NO—, —C≡C— or a single bond, or one of the radicals $R^1$ and $R^2$ is only F, Cl, Br, CN, NCS, NC or $SF_5$, c) if one of the rings $A^1$, $A^2$ and $A^3$ is a 2,3-difluoro-1,4-phenylene group and the other rings $A^1$, $A^2$ and $A^3$ are 1,4-phenylene groups, at least one group $Z^1$ and $Z^2$ is other than a single bond, or one of the radicals $R^1$ and $R^2$ is only F, Cl, Br, CN, NCS, NC or $SF_5$, and d) if one of the rings $A^1$, $A^2$ and $A^3$ is a 2,3-difluoro-1,4-phenylene group, one of the rings $A^1$, $A^2$ and $A^3$ is a 1,4-phenylene group and one of the rings $A^1$, $A^2$ and $A^3$ is a cyclohexylene group, at least one group $Z^1$ and $Z^2$ is other than a single bond.

For simplicity, in the following text Cyc is a 1,4-cyclohexylene group, CCN is a 1-(4)-cyano-1,4-cyclohexylene group, Che is a 1,4-cyclohexylene group, Dio is a 1,3-dioxane-2,5-diyl group, Dit is a 1,3-dithiane-2,5-diyl group, Bco is a 1,4-bicyclo[2.2.2]octylene group, Pip is a piperidine-1,4-diyl group, Phe is a 1,4-phenylene group, Pyd is a pyridine-2,5-diyl group, Pyr is a pyrimidine-2,5-diyl group and Pyn is a pyridazine-2,5-diyl group, it being possible for these groups to be unsubstituted or substituted. PheX is a group of the formula

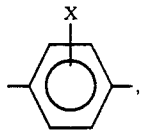

wherein X is preferably chlorine or fluorine. PheX$_2$ is a group of the formula

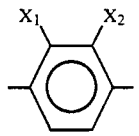

wherein $X_1$ and $X_2$ are preferably chlorine and/or fluorine.

The compounds of the formula I can be used as components of liquid crystal phases, in particular for displayed based on the principle of the twisted cell, the guest-host effect, the effect of deformation of aligned phases or the effect of dynamic scattering.

Compounds of the formula I having negative anisotropy of the dielectric constant ($\Delta\epsilon=\epsilon_{\parallel}-\epsilon_{\perp}<0$, $\epsilon_{\parallel}$ being the dielectric constant along the longitudinal molecular axis and $\epsilon_{\perp}$ being the dielectric constant perpendicular thereto) are aligned in an electrical field with their longitudinal molecular axes perpendicular to the direction of the field. This effect is known and is utilized for controlling optical transparency in various liquid crystal displays, thus, for example, in liquid crystal cells of the light scattering type (dynamic scattering), of the so-called DAP type (deformation of aligned phases) or of the guest/host type (guest/host interaction).

When a liquid crystal having positive dielectric anisotropy is used, homogeneous orientation thereof (which is achieved by treatment of the plate surface) is adjusted homoeotropically by applying a voltage, that is to say the cell is switched from "colored" to "colorless". Colorless symbols are displayed on a colored background in this way. In contrast, when a liquid crystal of negative dielectric anisotropy is used, homoeotropic orientation thereof is adjusted (by treatment of the plate surface) by applying a voltage parallel to the electrode surfaces, which allows display of coloured pictorial elements on a colourless background.

Two-frequency matrix addressing has furthermore been proposed to improve the multiplex circumstances in multiplex activation of liquid crystal displays, in particular of twisted cells and guest/host cells (for example German Offenlegungsschriften 28 56 134 and 29 07 940).

The fact that the dielectric anisotropy of liquid crystals which have positive anisotropy of the dielectric constant on application of a low-frequency voltage becomes negative under high frequencies is utilized here. In order to keep the capacitive losses small, the "crossover frequency" $f_c$ (dielectric relaxation frequency at which $\epsilon_{81}$ becomes $\epsilon_\perp$) of such liquid crystals should be as low as possible and should not be above, for example, 20 kHz. The absolute value of the dielectric anisotropy should furthermore be as large as possible both below and above the cross-over frequency. It has been found, however, that the substances which are particularly suitable for the two-frequency method in general have a lower absolute dielectric anisotropy at frequencies above the cross-over frequency than at those below the cross-over frequency. This disadvantages could be eliminated by addition of compounds having negative dielectric anisotropy and suitable relaxation properties.

Compounds of the formula I are furthermore suitable as compounds of chirally tilted smectic phases.

Chirally tilted smectic liquid crystal phases with ferroelectric properties can be prepared by adding a suitable chiral doping substance to base mixtures containing one or more tilted smectic phases (L. A. Veresnev et al., Mol. Cryst. Liq. Cryst. 89, 327 (1982); and H. R. Brand et al., J. Physique 44 (Lett.), L-771 (1983)). Such phases can be used as dielectrics for fast-switching displays based on the principle, described by Clark and Lagerwall, of SSFLC technology (N. A. Clark and S. T. Lagerwall, Appl. Phys. Lett. 36, 899 (1980); and U.S. Pat. No. 4,367,924) on the basis of the ferroelectric properties of the chirally tilted phase.

A number of liquid crystal compounds having weakly negative dielectric anisotropy have already been synthesized to date. In contrast, still relatively few liquid crystal components having high negative anisotropy of the dielectric constant are known. In addition, the latter in general have disadvantages such as, for example, poor solubility in mixtures, high viscosity, high melting points and chemical instability. There is therefore a need for further compounds having negative dielectric anisotropy, which enable the properties of mixtures for the most diverse electrooptical applications to be further improved.

Liquid crystal components having negative dielectric anisotropy and containing two or three rings linked via carboxyl groups or a covalent bond and one or more side groups, such as halogen, cyano or nitro groups, are known from DE 22 40 864, DE 26 13 293, DE 28 35 662, DE 28 36 086 and EP 023,728.

The compounds claimed here are included in a wide formula in EP 084,194. However, no individual compounds of the formula according to the invention are mentioned therein. From the prior art, the expert has thus not been able either to deduce synthesis possibilities for the compounds claimed in a simple manner, or to recognize that the compounds according to the invention have predominantly favorably located mesophase ranges and are distinguished by a high negative dielectric anisotropy coupled with a low viscosity.

That publication also lacks any indication at all of the possibility of using the compounds according to the invention in displays based on SSFLC technology, since the compounds claimed therein have low smectic tendencies.

Dibenzoates of 2,3-dichlorohydroquinone are moreover known (for example Bristol et al., J. Org. Chem. 39, 3138 (1974), or Clanderman et al., J. Am. Chem. Soc. 97, 1585 (1975)), but these are monotropic or have very small mesophase ranges. The 4-hydroxy-2,3-dichlorobenzoates which are described by Eidenschink et al. (Angew. Chem. 89, 103 (1977)) also have only narrow mesophase ranges.

PCT/EP 87/00515 contains a general formula which also includes difluorophenyl compounds, and 4-ethoxy-4''-pentyl-2,3-difluoroterphenyl is described therein as a constituent of ECB mixtures.

Because of their high viscosity, the 4-alkyl-2,3-dichlorophenyl-4'-alkylbicyclohexyl-4-carboxylates known from DE OS 29 33 563 cannot be used industrially.

The invention was based on the object of discovering stable liquid crystal or mesogenic compounds having a high negative dielectric anisotropy and at the same time a low viscosity.

It has been found that the compounds of the formula I are outstandingly suitable as components of liquid crystal phases. In particular, stable liquid crystal phases having a broad mesophase range and a comparatively low viscosity can be prepared with the aid of these compounds.

The compounds of the formula I are furthermore suitable as components of chirally tilted smectic liquid crystal phases.

By providing the compounds of the formula I, the range of liquid crystal substances which are suitable under various technological aspects for the preparation of liquid crystal mixtures is moreover quite generally considerably widened.

The compounds of the formula I have a wide range of applications. Depending on the choice of the substituents, these compounds can be used as base materials from which liquid crystal phases are predominantly composed; however, compounds of the formula I can also be added to liquid crystal base materials from other classes of compound, for example in order to vary the dielectric and/or optical anisotropy and/or the viscosity and/or the spontaneous polarization and/or phase ranges and/or the tilt angle and/or the pitch of such a dielectric.

The compounds of the formula I are furthermore suitable as intermediates for the preparation of other substances which can be used as constituents of liquid crystal dielectrics.

The compounds of the formula I are colorless the pure state and form liquid crystal mesophases in a temperature range which is favorably located for electrooptical use. They are very stable towards chemicals, heat and light.

The invention thus relates to the compounds of the formula I, in particular the compounds of the formulae A, B and C

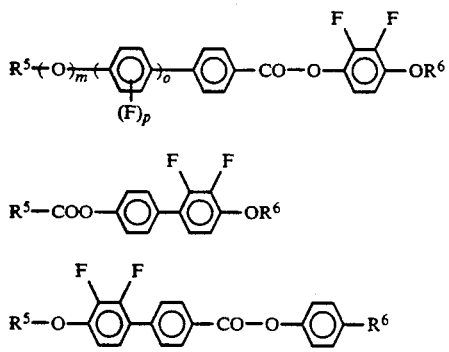

wherein $R^5$ and $R^6$ in each case independently of one another are alkyl having 1-15 C atoms and m, p and o are 0 or 1.

The invention furthermore relates to the use of the compounds of the formula I as components of liquid crystal phases. The invention moreover relates to liquid crystal phases containing at least one compound of the formula I and liquid crystal display elements containing such phases. Such phases have particularly advantageous elastic constants and, because of their low values, are particularly suitable for TFT mixtures.

Above and below, $R^1$, $R^2$, $A^1$, $A^2$, $A^3$, $Z^1$, $Z^2$ and n have the meaning given, unless expressly indicated otherwise.

The compounds of the formula I accordingly include compounds having two rings, of the part formulae Ia and Ib:

$$R^1—A^1—Z^1—A^2—R^2 \quad \text{Ia}$$

$$R^1—A^1—A^2—R^2 \quad \text{Ib,}$$

compounds having three rings, of the part formulae Ic to Ie:

$$R^1—A^1—A^2—A^3—R^2 \quad \text{Ic}$$

$$R^1—A^1—Z^1—A^2—A^3—R^2 \quad \text{Id}$$

$$R^1—A^1—Z^1—A^2—Z^2—A^3—R^2 \quad \text{Ie,}$$

compounds having four rings, of the part formulae If to Ik:

$$R^1—A^1—A^2—A^3—A^3—R^2 \quad \text{If}$$

$$R^1—A^1—Z^1—A^2—A^3—A^3—R^2 \quad \text{Ig}$$

$$R^1—A^1—A^2—Z^2—A^3—A^3—R^2 \quad \text{Ih}$$

$$R^1—A^1—Z^1—A^2—Z^2—A^3—A^3—R^2 \quad \text{Ii}$$

$$R^1—A^1—Z^1—A^2—A^3—Z^2—A^3—R^2 \quad \text{Ij}$$

$$R^1—A^1—Z^1—A^2—Z^2—A^3—Z^2—A^3—R^2 \quad \text{Ik}$$

and compounds having five rings, of the part formulae Il to It:

$$R^1—A^1—A^2—A^3—A^3—A^3—R^2 \quad \text{Il}$$

$$R^1—A^1—Z^1—A^2—A^3—A^3—A^3—R^2 \quad \text{Im}$$

$$R^1—A^1—A^2—Z^2—A^3—A^3—A^3—R^2 \quad \text{In}$$

$$R^1—A^1—Z^1—A^2—Z^2—A^3—A^3—A^3—R^2 \quad \text{Io}$$

$$R^1—A^1—Z^1—A^2—A^3—Z^2—A^3—A^3—R^2 \quad \text{Ip}$$

$$R^1—A^1—Z^1—A^2—A^3—A^3—Z^2—A^3—R^2 \quad \text{Iq}$$

$$R^1—A^1—Z^1—A^2—Z^2—A^3—Z^2—A^3—A^3—R^2 \quad \text{Ir}$$

$$R^1—A^1—Z^1—A^2—Z^2—A^3—A^3—Z^2—A^3—R^2 \quad \text{Is}$$

$$R^1—A^1—Z^1—A^2—Z^2—A^3—Z^2—A^3—Z^2—A^3—R^2 \quad \text{It.}$$

In the compounds of the formulae above and below, $R^1$ and $R^2$ are preferably alkyl, or furthermore alkoxy having 1-12 C atoms.

Compounds of the formulae above and below in which one of the radicals $R^1$ and $R^2$ is CN, F or Cl are furthermore preferred.

$A^1$, $A^2$ and $A^3$ are preferably PheX$_2$, Cyc, Phe, Dio or Pyr; the compound of the formula I preferably contains not more than in each case one of the radicals Dio, Dit, Pip, Bi, Pyn, Pyr or 2,3-dihalogeno-1,4-phenylene.

In accordance with the proviso that at least one of the rings $A^1$, $A^2$ and $A^3$ is 2,3-dihalogeno-1,4-phenylene, at least one of these rings can also be 2-fluoro-3-chloro-1,4-phenylene, 2-fluoro-3-bromo-1,4-phenylene, 2-fluoro-3-iodo-1,4-phenylene, 2-chloro-3-bromo-1,4-phenylene, 2-chloro-3-iodo-1,4-phenylene, 2-bromo-3-iodo-1,4-phenylene, 2,3-difluoro-1,4-phenylene, 2,3-dichloro-1,4-phenylene, 2,3-dibromo-1,4-phenylene or 2,3-diiodo-1,4-phenylene. The 2,3-dihalogeno-1,4-phenylene rings in which the halogen substituents are identical, such as 2,3-difluoro-1,4-phenylene or 2,3-dichloro-1,4-phenylene, are preferred here, and 2,3-difluoro-1,4-phenylene is particularly preferred.

n is preferably 0, 1 or 2, and particularly preferably 1.

The groups $Z^1$ and $Z^2$, which can be identical or different, are preferably single bonds, and secondly preferably —CO—O—, —O—CO—, —C≡C— or —CH$_2$CH$_2$— group. Particularly preferred compounds of the formula I are those wherein all the groups $Z^1$ and $Z^2$ are single bonds or only one group $Z^1$ or $Z^2$ is —CO—O—, —O—CO—, —C≡C— or —CH$_2$CH$_2$—.

In the case of 2,3-difluoro-1,4-phenylene compounds, the groups $Z^1$ or $Z^2$ adjacent to the PheX$_2$ group are preferably single bonds, —C≡C—, —O—CO—, —CO—O— or —CH$_2$CH$_2$— groups.

In the case of the 2,3-dichloro-1,4-phenylene compounds, the groups $Z^1$ or $Z^2$ adjacent to the PheX$_2$ group are preferably single bonds or —CO—O— or —O—CO— groups.

$R^1$ and $R^2$ in the formulae above and below preferably have 2-10 C atoms, in particular 3-7 C atoms. One or two CH$_2$ or CF$_2$ groups in $R^1$ and $R^2$ can also be replaced. Preferably, only one CH$_2$ group is replaced by —O—, —CO—, —C≡C—, —S—, —CH=CH—, —CH-halogeno- or —CHCN—, in particular by —O—, —CO— or —C≡C—.

In the formulae above and below, $R^1$ and $R^2$ are preferably alkyl, alkoxy or another oxaalkyl group, and furthermore also alkyl groups in which one or more CH$_2$ groups can be replaced by a grouping chosen from the group comprising —O—, —O—CO—, —C≡C—, —CH=CH—, —CH-halogeno- and —CHCN— or by a combination of two suitable groupings, hetero atoms not being linked directly to one another.

One of the radicals $R^1$ and $R^2$ is preferably also halogen or CN. Halogen is F, Cl or Br, preferably F. If none of the radicals $R^1$ and $R^2$ is halogen or CN, $R^1$ and $R^2$ together preferably have 4–16 C atoms, in particular 4–10 C atoms.

If $R^1$ and $R^2$ are alkyl radicals having in each case 4–14 C atoms, in which one ("alkoxy" or "oxaalkyl") or two ("alkoxyalkoxy" or "dioxaalkyl") non-adjacent CH$_2$ groups can be replaced by O atoms, they can be straight-chain or branched. Preferably, they are straight-chain and have 2, 3, 4, 5, 6 or 7 C atoms, and accordingly are preferably ethyl, propyl, butyl, pentyl, hexyl, heptyl, ethoxy, propoxy, butoxy, pentoxy, hexoxy or heptoxy, or furthermore methyl, octyl, nonyl, decyl, undecyl, dodecyl, tridecyl, tetradecyl, pentadecyl, methoxy, octyloxy, nonyloxy, decyloxy, undecyloxy, dodecyloxy, tridecyloxy or tetradecyloxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4-, 2,4-dioxapentyl, 1,3-, 1,4-, 1,5-, 2,4-, 2,5- or 3,5-dioxahexyl or 1,3-, 1,4-, 1,5-, 1,6-, 2,4-, 2,5-, 2,6-, 3,5-, 3,6- or 4,6- dioxaheptyl.

If $R^1$ and $R^2$ are an alkyl radical in which a CH$_2$ group is replaced by —S—, this can be straight-chain or branched. Preferably, this thiaalkyl radical having 1–10 C atoms is straight-chain and is 2-thiapropyl, 2 or 3-thiabutyl, 2-, 3- or 4- or 5-thiahexyl, 2-, 3-, 4-, 5- or 6-thiaheptyl, 2-, 3-, 4-, 5-, 6- or 7-thiaoctyl, 2-, 3-, 4-, 5-, 6-, 7- or 8-thianonyl or 2-, 3-, 4-, 5-, 6-, 7-, 8- or 9-thiadecyl.

Alkyl radicals $R^1$ or $R^2$ in which the CH$_2$ group adjacent to the group $A^1$, $A^2$ and/or $A^3$ is replaced by —S— and which are therefore preferably methylthio, ethylthio, propylthio, butylthio, pentylthio, hexylthio, heptylthio, octylthio, nonylthio or decylthio, are particularly preferred.

If $R^1$ and $R^2$ are an alkyl radical in which a CH$_2$ group is replaced by —CR$^3$=CR$^4$—, the radicals $R^3$ and $R^4$ are preferably identical and are hydrogen. This alkenyl radical can be straight-chain or branched. Preferably, it is straight-chain and has 2 to 10 C atoms. It is accordingly in particular vinyl, prop-1- or prop-2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl or dec-1-, -2-, -3-, -4-, -5-, -6-, -7-, -8- or -9-enyl.

If $R^1$ and $R^2$ are an alkyl radical in which a CH$_2$ group is replaced by —O—CO— or —CO—O—, this can be straight-chain or branched. Preferably, it is straight-chain and has 2 to 6 C atoms. It is accordingly in particular acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl and 4-(methoxycarbonyl)-butyl.

If $R^1$ and $R^2$ are an alkyl radical in which a CH$_2$ group is replaced by —CR$^3$=CR$^4$— and an adjacent CH$_2$ group is replaced by —CO—, —O—CO— or —O—CO—, $R^3$ and $R^4$ are preferably hydrogen or methyl.

Preferably, this (meth)acryloyloxyalkyl radical is straight-chain and has 4 to 13 C atoms. It is accordingly in particular cryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

Compounds of the formula I which have end group substituents $R^1$ and/or $R^2$ which are suitable for polymerization reactions are suitable for the preparation of liquid crystal polymers.

Compounds of the formula I having branched end group substituents $R^1$ and/or $R^2$ may occasionally be of importance because of a better solubility in the customary liquid crystal base materials, but in particular as chiral doping substances, if they are optically active. Smectic compounds of this type are suitable as components of ferroelectric materials.

Branched groups of this type as a rule contain not more than one chain branching. Preferred branched radicals $R^1$ and/or $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3oxa-4-methylpentyl, 4-methylhexyl, 2-nonyl, 2-decyl, 2-dodecyl, 6-methyloctoxy, 6-methyloctanoyloxy, 5-methylheptyloxycarbonyl, 2-methylbutyryloxy, 3-methylvaleryloxy, 4-methylhexanoyloxy, 2-chloropropionyloxy, 2-chloro-3-methylbutyryloxy, 2-chloro-4-methylvaleryloxy, 2-chloro-3-methylvaleryloxy, 2-methyl-3-oxapentyl, 2-methyl-3-oxahexyl, 2-fluoro-3-methylvaleryloxy and 2-fluoro-3-methylbutoxy.

If $R^1$ and $R^2$ are an alkyl radical in which two or more CH$_2$ groups are replaced by —O— and/or —CO—O—, this can be straight-chain or branched. Preferably, it is branched and has 3 to 12 C atoms. It is accordingly in particular bis-carboxy-methyl, 2,2-bis-carboxy-ethyl, 3,3-bis-carboxy-propyl, 4,4-bis-carboxybutyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl or 5,5-bis-)ethoxycarbonyl)-pentyl.

Compounds of the formula I which have end group substituents $R^1$ and/or $R^2$ which are suitable for polycondensation reactions are suitable for the preparation of liquid crystal polycondensates.

Formula I includes both the racemates of these compounds and the optical antipodes as well as mixtures thereof.

Of the compounds of the formulae I and Ia to It, those in which at least one of the radicals contained therein has one of the meanings given as preferred are preferred.

Of the dinuclear compounds of the part formulae Ia to Ib, those of the part formulae Iaa to Ial and Iba to Ibf are preferred:

| | |
|---|---|
| R¹—PheX₂—CH₂CH₂—Phe—R² | Iaa |
| R¹—PheX₂—CO—O—Phe—R² | Iab |
| R¹—PheX₂—O—CO—Phe—R² | Iac |
| R¹—PheX₂—C≡C—Phe—R² | Iad |
| R¹—PheX₂—CH₂CH₂—Cyc—R² | Iae |
| R¹—PheX₂—O—CO—Cyc—R² | Iaf |
| R¹—PheX₂—C≡C—Cyc—R² | Iag |
| R¹—PheX₂—CO—C—Cyc—R² | Iah |
| R¹—PheX₂—CH₂CH₂—PheX—R² | Iai |
| R¹—PheX₂—O—CO—PheX—R² | Iaj |
| R¹—PheX₂—O—CO—PheX—R² | Iak |
| R¹—PheX₂—C≡C—PheX—R² | Ial |
| R¹—PheX₂—Cyc—R² | Iba |
| R¹—PheX₂—Bco—R² | Ibb |
| R¹—PheX₂—Pyr—R² | Ibc |
| R¹—PheX₂—Pyd—R² | Ibd |
| R¹—PheX₂—Che—R² | Ibe |
| R¹—PheX₂—CCN—R² | Ibf |

Of the trinuclear compounds of the part formulae Ic to Ie, those of the part formulae Ica to Ieb are preferred:

| | |
|---|---|
| R¹—PheX₂—A²—A³—R² | Ica |
| R¹—A¹PheX₂—A³—R² | Icb |
| R¹—PheX₂—Z¹—A²—A³—R² | Ida |
| R¹—A¹—Z¹—PheX₂—A³—R² | Idb |
| R¹—A¹—Z¹—A²—PheX₂—R² | Idc |
| R¹—PheX₂—Z¹—A²—Z²—A³—R² | Iea |
| R¹—A¹—Z¹—PheX₂—Z²—A³—R² | Ieb |

Of the preferred compounds of the part formulae Ida to Idc, those of the part formulae Id1 to Id6 are particularly preferred:

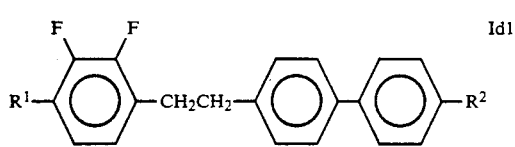
Id1

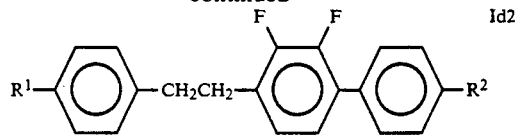
Id2

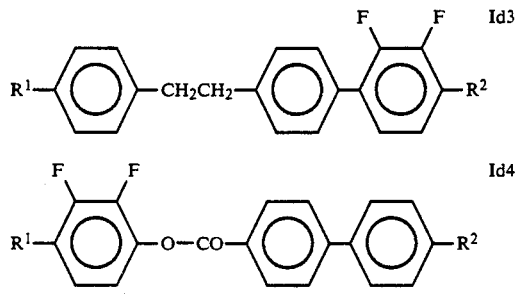
Id3

Id4

Id5

Id6

Of the tetranuclear compounds of the part formulae If to Ik, those of the part formulae I1 to I8 are preferred:

| | |
|---|---|
| R¹—PheX₂—A²—A³—A³—R² | I1 |
| R¹—A¹—PheX₂—A³—A³—R² | I2 |
| R¹—PheX₂—Z¹—A²—A³—A³—R² | I3 |
| R¹—A¹—Z¹—PheX₂—A³—A³—R² | I4 |
| R¹—A¹—Z¹—A²—PheX₂—A³—R² | I5 |
| R¹—A¹—Z¹—A²—A³—PheX₂—R² | I6 |
| R¹—PheX—A²—Z²—A³—A³—R² | I7 |
| R¹—A¹—PheX—Z²—A³—A³—R² | I8 |

In the above compounds of the part formulae Iaa to I8, PheX₂ is preferably 2,3-difluoro-1,4-phenylene or 2,3-dichloro-1,4-phenylene. The groups A¹, A² and A³ in the compounds of the part formulae Ica to I8 are preferably trans-1,4-cyclohexylene (Cyc), 1,4-cyclohexylene (Che), 1,4-phenylene (Phe), 1,4-bicyclo[2.2.2]-octylene (Bco), 2- or 3-halogeno-1,4-phenylene (PheX), dioxane-2,5-diyl (Dio), dithiane-2,5-diyl (Dit) or pyrimidine-2,5-diyl (Pyr). Those of the above-mentioned formulae which contain one or more groups CCN, Dio, Dit and/or Pyr in each case include the two possible 2,5-(Dio,Dit,Pyr) or 1,4-(CCN) position isomers.

The following small groups II to XVI of compounds in which PheX₂ is 2,3-difluoro-1,4-phenylene or 2,3-dichloro-1,4-phenylene are particularly preferred.

Alkyl is preferably straight-chain methyl, ethyl, propyl, butyl, pentyl, hexyl, heptyl, octyl, nonyl or decyl; and oxaalkyl is preferably straight-chain 2-oxapropyl (=methoxymethyl), 2-(=ethoxymethyl) or 3-oxabutyl (=2-methoxymethyl), 2-, 3- or 4-oxapentyl, 2-, 3-, 4- or 5-oxahexyl, 2-, 3-, 4-, 5or 6-oxaheptyl, 2-, 3-, 4-, 5-, 6- or 7-oxaoctyl, 2-, 3-, 4-, 5- , 6-, 7- or 8-oxanonyl or 2-, 3-, 4-, 5-, 6-, 7-, 8- or 9-oxadecyl.

Alkoxy is preferably straight-chain methoxy, ethoxy, propoxy, butoxy, pentoxy, hexoxy, heptoxy, octyloxy, nonyloxy or decyloxy.

Halogen is preferably chlorine or fluorine, particularly preferably fluorine.

II alkyl-PheX$_2$-Cyc-alkyl
alkyl-PheX$_2$-Cyc-alkoxy
alkyl-PheX$_2$-Cyc-CO-O-alkyl
alkyl-PheX$_2$-Cyc-O-CO-alkyl
halogeno-PheX$_2$-Cyc-alkyl
nitrile-PheX$_2$-Cyc-alkyl
halogeno-PheX$_2$-Cyc-CO-O-alkyl
alkyl-PheX$_2$-Cyc-oxaalkyl
alkyl-PheX$_2$-CCN-alkyl

III alkyl-PheX$_2$-Pry-alkyl
halogeno-PheX$_2$-Pyr-alkyl
nitrile-PheX$_2$-Pyr-alkyl
alkoxy-PheX$_2$-Pry-alkyl

IV alkyl-PheX$_2$-Cyc-Phe-alkyl
alkyl-PheX$_2$-Cyc-Phe-alkoxy
halogeno-PheX$_2$-Cyc-Phe-alkyl
alkyl-PheX$_2$-Cyc-Phe-CO-O-alkyl
alkyl-PheX$_2$-Cyc-Phe-O-CO-alkyl
alkyl-PheX$_2$-Cyc-Phe-CN
alkyl-PheX$_2$-Cyc-PheX-CN
alkyl-PheX$_2$-Phe-Cyc-alkyl
alkyl-PheX$_2$-Cyc-Cyc-alkyl
alkyl-PheX$_2$-Cyc-Cyc-CN
halogeno-PheX$_2$-Cyc-Cyc-alkyl
alkyl-Phe-PheX$_2$-Cyc-alkyl
alkyl-Phe-PheX$_2$-Cyc-CO-O-alkyl
nitrile-Phe-PheX$_2$-Cyc-alkyl
alkyl-PheX-PheX$_2$-Cyc-alkyl

V alkyl-PheX$_2$Phe-Phe-Cyc-alkyl
alkyl-PheX$_2$-Phe-Phe-Cyc-CN
alkyl-PheX$_2$-Cyc-Phe-Cyc-alkyl
halogeno-PheX$_2$-Cyc-Phe-Cyc-alkyl
alkyl-Phe-Cyc-PheX$_2$-Cyc-alkyl
alkyl-PheX-Cyc-PheX$_2$-Cyc-alkyl
nitrile-PheX-Cyc-PheX$_2$-Cyc-alkyl
nitrile-Phe-Cyc-PheX$_2$-Cyc-CO-O-alkyl

VI alkyl-PheX$_2$-CO-O-Phe-alkyl
alkyl-PheX$_2$-CO-O-Phe-CN
alkyl-PheX$_2$-CO-O-Phe-SF$_5$
alkyl-PheX$_2$-O-CO-Phe-alkyl
alkyl-PheX$_2$-O-CO-Phe-alkoxy
alkyl-PheX$_2$-CH$_2$CH$_2$-Phe-alkyl
alkyl-PheX$_2$X$_2$-CH$_2$CH$_2$-Phe-CN
halogeno-PheX$_2$-CH$_2$CH$_2$-Phe-alkyl
alkyl-PheX$_2$-CH$_2$CH$_2$-Phe-alkoxy
alkyl-PheX$_2$-CH$_2$CH$_2$-Phe-alkyl
halogeno-PheX$_2$-O-CO-Phe-alkyl

VII alkyl-PheX$_2$-CH$_2$CH$_2$-PheX-CN
halogeno-PheX$_2$-CH$_2$CH$_2$-PheX-CN
alkyl-PheX$_2$-CO-O-PheX-alkyl
alkyl-PheX$_2$-O-CO-PheX-alkyl

VIII alkyl-PheX$_2$-CO-O-Cyc-alkyl
alkyl-PheX$_2$-O-CO-Cyc-alkyl
halogenc-PheX$_2$-O-CO-Cyc-alkyl
alkyl-PheX$_2$-CH$_2$CH$_2$-Cyc-alkyl
alkyl-PheX$_2$-CH$_2$CH$_2$-Dio-alkyl
alkyl-PheX$_2$-C≡C-Cyc-CN

IX alkyl-PheX$_2$-CO-O-Phe-Phe-alkyl
alkyl-PheX$_2$-CO-O-Phe-Phe-alkoxy
alkyl-PheX$_2$-I-CO-Phe-Phe-alkyl
alkyl-PheX$_2$-CH$_2$CH$_2$Phe-Phe-alkyl
halogeno-PheX$_2$-CH$_2$CH$_2$-Phe-Phe-alkyl
halogeno-PheX$_2$-O-CO-Phe-Phe-alkyl
nitrile-PheX$_2$-CO-O-Phe-Phe-alkyl
Alkyl-PheX$_2$-CH$_2$CH$_2$-Phe-Phe-CN
Alkyl-PheX$_2$-CH$_2$CH$_2$-Phe-Phe-Halogen
Alkoxy-PheX$_2$-CH$_2$CH$_2$-Phe-Phe-Halogen
Alkoxy-PheX$_2$-CH$_2$CH$_2$-Phe-Phe-CN
Alkoxy-PheX$_2$-CH$_2$CH$_2$-Phe-Phe-Alkyl
Nitril-PheX$_2$-CH$_2$CH$_2$-Phe-Phe-Alkyl

X alkyl-PheX$_2$-CO-O-Cyc-Phe-alkyl
alkyl-PheX$_2$-CO-O-Phe-Cyc-alkyl
halogeno-PheX$_2$-CO-O-Phe-Cyc-alkyl
halogeno-PheX$_2$-O-CO-Cyc-Phe-alkyl
alkyl-PheX$_2$-CH$_2$CH$_2$-Phe-Cyc-alkyl
alkyl-PheX$_2$-CH$_2$CH$_2$-Phe-Cyc-CN
nitrile-PheX$_2$-CO-O-Phe-Cyc-alkyl
alkyl-PheX$_2$-O-CO-Phe-Cyc-alkyl
alkyl-PheX$_2$-O-CO-Cyc-Phe-alkyl
halogeno-PheX$_2$-O-CO-Cyc-Phe-alkyl

XI alkyl-PheX$_2$-CO-O-Cyc-Cyc-alkyl
alkyl-PheX$_2$-O-CO-Cyc-Cyc-alkyl
halogeno-PheX$_2$-O-CO-Cyc-Cyc-alkyl
alkyl-PheX$_2$-CH$_2$CH$_2$-Cyc-Cyc-alkyl
alkyl-PheX$_2$-CH$_2$CH$_2$-Cyc-CCN-alkyl

XII alkyl-PheX$_2$-CH$_2$CH$_2$-Pyd-Phe-alkoxy
alkyl-PheX$_2$-CO-O-Phe-Pyd-alkyl

XIII alkyl-Phe-CO-O-PheX$_2$Phe-alkyl
alkyl-Phe-CH$_2$CH$_2$-PheX$_2$-Phe-alkyl
halogeno-Phe-CO-O-PheX$_2$-Phe-alkyl
halogeno-Phe-O-CO-PheX$_2$-Phe-alkyl
alkyl-Cyc-CH$_2$CH$_2$-PheX$_2$-Phe-alkyl
alkyl-Phe-CH$_2$CH$_2$-PheX$_2$-Cyc-alkyl
alkyl-Cyc-CH$_2$CH$_2$-PheX$_2$-Cyc-alkyl
Alkyl-Phe-CH$_2$CH$_2$-PheX$_2$-Phe-Alkoxy
Alkyl-Phe-CH$_2$CH$_2$-PheX$_2$-Phe-CN
Alkyl-Phe-CH$_2$CH$_2$-PheX$_2$-Phe-Halogen
Alkoxy-Phe-CH$_2$CH$_2$-PheX$_2$-Phe-Halogen
Alkoxy-Phe-CH$_2$CH$_2$-PheX$_2$-Phe-CN
Alkoxy-Phe-CH$_2$CH$_2$-PheX$_2$-Phe-Alkyl
Nitril-Phe-CH$_2$CH$_2$-PheX$_2$-Phe-Alkyl

XIV alkyl-PheX$_2$-Phe-CO-O-Phe-halogeno
alkyl-PheX$_2$-Phe-CO-O-Phe-alkyl
alkyl-PheX$_2$-Phe-CH$_2$CH$_2$-Phe-alkyl
alkyl-PheX$_2$-Phe-CH$_2$CH$_2$-Cyc-alkyl
alkyl-PheX$_2$-Cyc-CH$_2$CH$_2$-Phe-alkyl
alkyl-PheX$_2$-Cyc-CH$_2$CH$_2$-Cyc-alkyl
Alkyl-PheX$_2$-Phe-CH$_2$CH$_2$-Phe-Alkyl
Alkyl-PheX$_2$-Phe-CH$_2$CH$_2$-Phe-Halogen
Alkyl-PheX$_2$-Phe-CH$_2$CH$_2$-Phe-CN
Alkyl-PheX$_2$-Phe-CH$_2$CH$_2$-Phe-Alkoxy
Nitril-PheX$_2$-Phe-CH$_2$CH$_2$-Phe-Alkoxy
Halogen-PheX$_2$-Phe-CH$_2$CH$_2$-Phe-Alkoxy
Halogen-PheX$_2$-Phe-CH$_2$CH$_2$-Phe-Alkyl
Nitril-PheX$_2$-Phe-CH$_2$CH$_2$-Phe-Alkyl

XV alkyl-PheX$_2$-CO-O-Phe-CO-O-Phe-alkyl
halogeno-PheX$_2$-CO-O-Phe-CO-O-Phe-alkyl
halogeno-PheX$_2$-CO-O-Phe-O-CO-Phe-alkyl
alkyl-PheX$_2$-CO-O-Phe-O-CO-Phe-alkyl
alkyl-Phe-CO-O-PheX$_2$-O-CO-Phe-alkyl
halogeno-Phe-CO-O-PheX$_2$-O-CO-Phe-alkyl
halogeno-Phe-CO-O-PheX$_2$-OCO-Cyc-alkyl
alkyl-Phe-CO-O-PheX$_2$-OCO-Cyc-alkyl
halogeno-PheX$_2$-OCH$_2$-Cyc-Cyc-alkyl
halogeno-PheX$_2$-OCH$_2$-Cyc-CH$_2$CH$_2$-Cyc-alkyl
alkoxy-PheX$_2$-OCH$_2$-Cyc-CH$_2$CH$_2$-Phe-alkyl
alkoxy-PheX$_2$-OCH$_2$Phe-CH$_2$CH$_2$-Phe-alkyl
alkoxy-PheX$_2$-OCH$_2$-Phe-CO-O-Phe-alkyl
alkoxy-PheX$_2$-OCH$_2$-Cyc-CO-O-Phe-alkyl
alkoxy-PheX$_2$-OCH$_2$-Cyc-CH$_2$CH$_2$-Cyc-alkyl The compounds of he formula I are prepared by methods which are known per se, such as are described in the literature (for example in the standard works, such as Houben-Weyl, Methoden der Organischen Chemie (Methods of Organic Chemistry), Georg-Thieme-Verlag, Stuttgart), and in particular under reaction conditions which are known and suitable for the reactions mentioned. In these reactions, it is also possible to utilize variants which are known per se but are not mentioned here in more detail.

If desired, the starting substances can also be formed in situ such that they are not isolated from the reaction mixture but are immediately reacted further to give the compounds of the formula I.

Compounds of the formula I wherein one of the groups A$^1$, A$^2$ or A$^3$ is 2,3-difluoro-1,4-phenylene are accessible starting from 1,2-difluoro-benzene.

This is metallized by known processes (for example A. M. Roe et al., J. Chem. Soc. Chem. Comm., 22, 582 (1965)) and the product is reacted with the corresponding electrophile. This reaction sequence can be carried out a second time on the 1-substituted 2,3-difluorobenzene thus obtained and 1,4-disubstituted 2,3-difluorobenzene derivatives of the formula I are in this way obtained. The 1,2-difluorobenzene or 1-substituted 2,3-difluorobenzene is reacted with phenyllithium, lithiumtetramethylpiperidine or n-, sec.- or tert.-butyllithium in an inert solvent, such as diethyl ether, tetrahydrofuran, dimethoxyethane, tert.-butyl methyl ether or dioxane, hydrocarbons, such as hexane, heptane, cyclohexane, benzene or toluene, or mixtures of these solvents, if appropriate with the addition of a complexing agent, such as tetramethylethylenediamine or hexamethylphosphoric acid triamide, at temperatures of −100° C. to +50° C., preferably −78° C. to 0° C.

The lithium-2,3-difluorophenyl compounds are reacted with the corresponding electrophiles at −100° C. to 0° C., preferably at −50° C. Suitable electrophiles are aldehydes, ketones, nitriles, epoxides, carboxylic acid derivatives, such as esters, anhydrides or halides, halogenoformic acid esters or carbon dioxide.

For reaction with aliphatic or aromatic halogen compounds, the lithium-2,3-difluorophenyl compounds are transmetallized and the products are coupled under transition metal catalysis. The zinc- (compare DE OS 36 32 410) or the titanium-2,3-difluorophenyl compounds (compare DE OS 37 36 489) are particularly suitable for this.

The compounds of the formula I can be prepared by reducing a compound which otherwise corresponds to the formula I but contains one or more reducible groups and/or C—C bonds instead of H atoms.

Preferred possible reducible groups are carbonyl groups, in particular keto groups, and furthermore, for example, free or esterified hydroxyl groups or aromatically bonded halogen atoms. Preferred starting substances for the reduction correspond to the formula I, but can contain a cyclohexene ring or cyclohexanone ring instead of a cyclohexane ring and/or a —CH=CH— group instead of a —CH$_2$CH$_2$— group and/or a —CO— group instead of a —CH$_2$— group and/or a free or a functionally modified (for example in the form of its p-toluenesulfonate) OH group instead of an H atom.

The reduction can be carried out, for example, by catalytic hydrogenation at temperatures between about 0° and about 200° under pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Catalysts which are advantageously suitable are noble metals, such as Pt or Pd, which can be used in the form of oxides (for example PtO$_2$ or PdO), on a support (for example Pd-on-charcoal, -calcium carbonate or -strontium carbonate) or in finely divided form.

Ketones can also be reduced by the Clemmensen method (using zinc, amalgamated zinc or tin and hydrochloric acid, advantageously in aqueous-alcohol solution or in a heterogeneous phase system using water/toluene at temperatures between about 80° and 120°) or the Wolff-Kishner method (using hydrazine, advantageously in the presence of an alkali, such as KOH or NaOH, in a high-boiling solvent, such as diethylene glycol or triethylene glycol, at temperatures between about 100° and 200°) to give the corresponding compounds of the formula I containing alkyl groups and/or —CH$_2$CH$_2$— bridges.

Reductions using complex hydrides are furthermore possible. For example, arylsulfonyloxy groups can be removed by reduction with LiAlH$_4$, and in particular p-toluenesulfonyloxymethyl groups can be reduced to methyl groups, advantageously in an inert solvent, such as diethyl ether or THF, at temperatures between about 0° and 100°. Double bonds (also in the presence of CN groups) can be hydrogenated with NaBH$_4$ or tributyltin hydride in methanol.

Esters of the formula I can also be obtained by esterification of corresponding carboxylic acids (or their reactive derivatives) with alcohols or phenols (or their reactive derivatives).

Particularly suitable reactive derivatives of the carboxylic acids mentioned are the acid halides, above all the chlorides and bromides, and furthermore the anhydrides, for example also mixed anhydrides, azides or esters, in particular alkyl esters having 1-4 C atoms in the alkyl group.

Possible reactive derivatives of the alcohols and phenols mentioned are, in particular, the corresponding metal alcoholates and phenolates, preferably of an alkali metal, such as Na or K.

The esterification is advantageously carried out in the presence of an inert solvent. Particularly suitable solvents are ethers, such as diethyl ether, di-n-butyl ether, THF, dioxane or anisole, ketones, such a acetone, butanone or cyclohexanone, amides, such as DMF or phosphoric acid hexamethyltriamide, hydrocarbons, such as benzene, toluene or xylene, halogenohydrocarbons, such as carbon tetrachloride or tetrachloroethylene, and sulfoxides, such as dimethyl sulfoxide or sulfolane. Water-immiscible solvents can advantageously be used at the same time for azeotropic removal by distillation of the water formed during the esterification. An excess of an organic base, for example pyridine, quinoline or triethylamine, may occasionally also be used as the solvent for the esterification. The esterification can also be carried out in the absence of a solvent, for example by simply heating the components in the presence of sodium acetate. The reaction temperature is usually between $-50°$ and $+250°$, preferably between $-20°$ and $+80°$. At these temperatures, the esterification reactions are as a rule ended after 15 minutes to 48 hours.

In detail, the reaction conditions for the esterification largely depend on the nature of the starting substances used. Thus, a free carboxylic acid is as a rule reacted with a free alcohol or phenol in the presence of a strong acid, for example, a mineral acid, such as hydrochloric acid or sulfuric acid. A preferred reaction procedure is to react an acid anhydride or, in particular, an acid chloride with an alcohol, preferably in a basic medium, bases which are of importance being, in particular, alkali metal hydroxides, such as sodium hydroxide or potassium hydroxide, alkali metal carbonates or bicarbonates, such as sodium carbonate, sodium bicarbonate, potassium carbonate or potassium bicarbonate, alkali metal acetates, such as sodium acetate or potassium acetate, alkaline earth metal hydroxides, such as calcium hydroxide, or organic bases, such as triethylamine, pyridine, lutidine, collidine or quinoline. Another preferred embodiment of the esterification comprises a procedure in which the alcohol or phenol is first converted into the sodium or potassium alcoholate or phenolate, for example by treatment with ethanolic sodium hydroxide solution or potassium hydroxide solution, this alcoholate or phenolate is isolated and suspended in acetone or diethyl ether together with sodium bicarbonate or potassium carbonate, while stirring, and a solution of acid chloride or anhydride in diethyl ether, acetone or DMF is added to this suspension, advantageously at temperatures between about $-25°$ and $+20°$.

To prepare nitriles of the formula I (wherein $R^1$ and/or $R^2$ are CN and/or wherein $A^1$, $A^2$ and/or $A^3$ is substituted by at least one CN group), corresponding acid amides, for example those in which the radical X is replaced by a $CONH_2$ group, can be dehydrated. The amides are obtainable, for example, from corresponding esters or acid halides by reaction with ammonia. Examples of suitable dehydrating agents are inorganic acid chlorides such as $SOCl_2$, $PCl_3$, $PCl_5$, $POCl_3$, $SO_2Cl_2$ or $COCl_2$, and furthermore $P_2O_5$, $P_2S_5$, $AlCl_3$ (for example as a double compound with NaCl), aromatic sulfonic acids and sulfonic acid halides. This reaction can be carried out in the presence or absence of an inert solvent at temperatures between about 0° and 150°; possible solvents are, for example, bases, such as pyridine or triethylamine, aromatic hydrocarbons, such as benzene, toluene or xylene, or amides, such as DMF.

To prepare the abovementioned nitriles of the formula I, corresponding acid halides, preferably the chlorides, can also be reacted with sulfamide, advantageously in an inert solvent, such as tetramethylensulfone, at temperatures between about 80° and 150°, preferably at 120°. After customary working up, the nitriles can be isolated directly.

Ethers of the formula I (wherein $R^1$ and/or $R^2$ is an alkoxy group and/or wherein $Z^1$ and/or $Z^2$ is a $—OCH_2—$ or a $—CH_2O—$ group) are obtainable by etherification of corresponding hydroxy compounds, preferably corresponding phenols, the hydroxy compound advantageously first being converted into the corresponding metal derivative, for example into the corresponding alkali metal alcoholate or alkali metal phenolate by treatment with NaH, $NaNH_2$, NaOH, KOH, $Na_2CO_3$ or $K_2CO_3$. this derivative can then be reacted with the corresponding alkyl halide or sulfonate or dialkyl sulfate, advantageously in an inert solvent, such as acetone, 1,2-dimethoxyethane, dimethylformamide or dimethyl sulfoxide or an excess of aqueous or aqueous-alcoholic NaOH or KOH, at temperatures between about 20° and 100°.

To prepare nitriles of the formula I (wherein $R^1$ and/or $R^2$ is CN and/or wherein $A^1$, $A^2$ and/or $A^3$ is substituted by at least one CN group), corresponding chlorine or bromine compounds of the formula I (wherein $R^1$ and/or $R^2$ is Cl or Br and/or wherein $A^1$, $A^2$ and/or $A^3$ is substituted by at least one Cl or Br atom) can also be reacted with a cyanide, advantageously with a metal cyanide, such as NaCN, KCN or $Cu_2(CN)_2$, for example in the presence of pyridine, in an inert solvent, such as dimethylformamide or N-methylpyrrolidone, at temperatures between 20° and 200°.

Compounds of the formula I wherein $R^1$ or $R^2$ is F, Cl, Br or CN can also be obtained from the corresponding diazonium salts by replacement of the diazonium group by a fluorine, chlorine or bromine atom or by a CN group, for example by the methods of Schiemann or Sandmeyer.

The diazonium salts can be prepared, for example, by nitration of compounds which correspond to the formula I but contain one (or two) hydrogen atom(s) instead of the radicals $R^1$ and/or $R^2$, reduction to the corresponding amines and diazotization, for example with $NaNO_2$ or $KNO_2$ in aqueous solution at temperatures between about $-10°$ and $+10°$.

To replace the diazonium group by fluorine, the compounds can be diazotized in anhydrous hydrofluoric acid and then heated, or they are reacted with tetrafluoboric acid to give the diazonium tetrafluoborates, which are then decomposed by heat.

Replacement by Cl, Br or CN is advantageously effected by reaction of the aqueous diazonium salt solution with $Cu_2Cl_2$, $Cu_2Br_2$ or $Cu_2(CN)_2$ by the Sandmeyer method.

Compounds of the formula I wherein $R^1$ or $R^2$ is $SF_5$ can be prepared in accordance with DE-OS 37 21 268. Isothiocyanates of the formula I wherein $R^1$ or $R^2$ is —NCS are prepared in accordance with DE-OS 37 11 510. The isonitriles of the formula I wherein $R^1$ or $R^2$ is —CN are prepared by a method analogous to that in DE-OS 36 33 403.

The tolanes and alkyne compounds ($R^1$ and/or $R^2$ is an alkyl group, one or more $CH_2$ groups being replaced by —C≡C—, or $Z^1$ and/or $Z^2$=—C≡C—) are prepared, for example, by reaction of the corresponding halogen compound with an acetylide in a basic solvent under transition metal catalysis; palladium catalysts can preferably be used here, in particular a mixture of bis-(triphenylphosphine)palladium(II) chloride and copper iodide in piperidine as the solvent.

The liquid crystal phases according to the invention preferably contain 2 to 40, in particular 4 to 30, components as other constituents in addition to one or more compounds according to the invention. These phases especially preferably contain 7 to 25 components in addition to one or more compounds according to the invention. These other constituents are preferably chosen from the nematic or nematogenic (monotropic or isotropic) substances, in particular substances from the classes of azoxybenzenes, benzylideneanilines, biphenyls, terphenyls, phenyl or cyclohexyl benzoates, phenyl or cyclohexyl cyclohexanecarboxylates, phenyl or cyclohexyl cyclohexylbenzoates, phenyl or cyclohexyl cyclohexanecarboxylates, cyclohexylphenyl benzoates, cyclohexanecarboxylate or cyclohexylcyclohexanecarboxylate, phenylcyclohexanes, cyclohexylbiphenyls, phenylcyclohexylcyclohexanes, cyclohexylcyclohexanes, cyclohexylcyclohexenes, cyclohexylcyclohexylcyclohexes, 1,4-bis-cyclohexylbenzenes, 4,4'-bis-cyclohexylbiphenyls, phenyl- or cyclohexyl-pyrimdines, phenyl- or cyclohexyl-pyridinesd, phenyl- or cyclohexyl-dioxanes, phenyl- or cyclohexyl-1,3-dithianes, 1,2-diphenylethanes, 1,2-dicyclohexnylethanes, 1-phenyl-2-cyclohexnylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolanes and substituted cinnamic acids. The 1,4-phenylene groups in these compounds can also be fluorinated.

The most important compounds possible as other constituents of the phases according to the invention can be characterized by the formulae 1, 2, 3, 4 and 5:

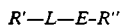
R'—L—E—R"  1

R'—L—COO—E—R"  2

R'—L—OOC—E—R"  3

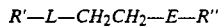
R'—L—CH₂CH₂—E—R"  4

R'—L—C≡C—E—R"  5

In the formulae 1, 2, 3, 4 and 5, L and E, which can be identical or different, in each case independently of one another are a bivalent radical from the group comprising —Phe—, —Cyc—, —Phe—Phe—, —Phe—Cyc—, —Cyc—Cyc—, —Pyr—, —Dio—, —G—Phe— and —G—Cyc— and mirror images thereof, wherein Phe is 1,4-phenylene which is unsubstituted or substituted by fluorine, Cyc is trans-1,4-cyclohexylene or 1,4-cyclohexylene, Pyr is pyrimidine-2,5-diyl or pyrimidine-2,5-diyl, Dio is 1,3-dioxane-2,5-diyl and G is 2-(trans-1,4-cyclohexyl)-ethyl, pyrimidine-2,5-diyl, pyridine-2,5-diyl or 1,3-dioxane-2,5-diyl.

Preferably, one of the radicals L and E is Cyc, Phe or Pyr. E is preferably Cyc, Phe or Phe—Cyc. The phases according to the invention preferably contain one or more components chosen from the compounds of the formula 1, 2, 3, 4 and 5 wherein L and E are chosen from the group comprising Cyc, Phe and Pyr and at the same time one or more components chosen from the compounds of the formulae 1, 2, 3, 4 and 5 wherein one of the radicals L and E is chosen from the group comprising Cyc, Phe and Pyr and the other radical is chosen from the group comprising —Phe—Phe—, —Phe—Cyc—, —Cyc—Cyc—, —G—Phe— and —G—Cyc—, and if appropriate one or more components chosen from the compounds of the formulae 1, 2, 3, 4 and 5 wherein the radicals L and E are chosen from the group comprising —Phe—Cyc—, —Cyc—Cyc—, —G—Phe— and —G—Cyc—.

R' and R" in the compounds of the part formulae 1a, 2a, 3a, 4a and 5a in each case independently of one another are alkyl, alkenyl, alkoxy, alkenyloxy or alkanoyloxy having up to 8 carbon atoms. In mose of these compounds, R' and R" differ from one another, one of these radicals usually being alkyl or alkenyl. In the compounds of the part formulae 1b, 2b, 3b, 4b, and 5b, R" is —CN, —CF₃, F, Cl or —NCS; R here has the meaning given in the case of the compounds of the part formulae 1a to 5a, and is preferably alkyl or alkenyl. However, other variants of the envisaged substituents in the compounds of the formulae 1, 2, 3, 4, and 5 can also be used. Many such substances or even mixtures thereof are commercially available. All these substances are obtainable by methods which are known from the literature or by analogous methods.

The phases according to the invention preferably also contain, in addition to components from the group of compounds 1a, 2a, 3a, 4a and 5a (group 1), components from the group of compounds 1b, 2b, 3b, 4b and 5b (group 2), the proportions of which are preferably as follows:

Group 1: 20 to 90%, in particular 30 to 90%,
Group 2: 10 to 80%, in particular 10 to 50%,
the sum of the proportions of the compounds according to the invention and the compounds from groups 1 and 2 making up to 100%.

The phases according to the invention preferably contain 1 to 40%, particularly preferably 5 to 30%, of compounds according to the invention. Phases containing more than 40%, in particular 45 to 90%, of compounds according to the invention are furthermore preferred. The phases preferably contain three, four or five compounds according to the invention.

The phases according to the invention are prepared in a manner which is customary per se. As a rule, the components are dissolved in one another, advantageously at elevated temperature. The liquid crystal phases according to the invention can be modified by suitable additives so that they can be used in all the types of liquid crystal display elements disclosed to date. Such additives are known to the expert and are described in detail in the literature (H. Kelker/R. Hatz, Handbook of Liquid Crystals, Verlag Chemie, Weinheim, 1980). For example, it is possible to add pleochroic dyestuffs to prepare colored guest-host systems or substances for modifying the dielectric anisotropy, the viscosity and/or the orientation of the nematic phases.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding application West German P 38 07 908.9, filed Mar. 10, 1988, are hereby incorporated by reference.

"Customary working up" means: water is added, the mixture is extracted with methylene chloride, the organic phase is separated off, dried and evaporated and the product is purified by crystallization and/or chromatography.

Further abbreviations have the following meanings: C: crystalline-solid state; S: smectic phase (the index identifies the phase type); N: nematic state; Ch: chloesteric phase; I: isotropic phase. The number between two symbols indicates the transition temperature in degrees Celsius.

EXAMPLES

Example 1

A mixture of 10 mmol of dicyclohexylcarbodiimide and 1.5 ml of toluene is added to a amixture of 10 mmol of p-pentylbenzoic acid, 10 mmol 2,3,4-trifluorophenol (prepared from 1,2,3-trifluorobenzene in accordance with the literature: A. M. Roe et al., Chem. Comm. 1965, 582, by metalation with n-butyllithium at $-50°$ C. analogously to Example 2 and subsequent oxygenation with atmospheric oxygen), 1 mmol of 4-dimethylaminopyridine and 15.0 ml of toluene. After the mixture has been stirred at room temperature for 4 hours, 20 mg of oxalic acid are added and the mixture is stirred for a further 30 minutes. Customary working up gives 2,3,4-trifluorophenyl p-pentylbenzoate.

Example 2

12.5 ml of a 0.8 molar solution of n-butyllithium in hexane/tetrahydrofuran (1:1) are added to a mixture of 10 mmol of 1,2,3-trifluorobenzene and 5 ml of tetrahydrofuran at $-78°$ C. After the reaction mixture has been warmed to $-50+$ C., it is stirred for 7 hours. The carboxylic acid obtained after introducing dried, gaseous carbon dioxide, acidifiation and customary working up is treated with trans-4-pentylcyclohexanol analogously to Example 14. Customary working up gives trans-4-pentylcyclohexyl 2,3,4-trifluorobenzoate.

Example 3

A mixture of 10 mmol of 1-(2,3,4-trifluorophenyl)-4-propylcyclohex-1-ene (prepared from 2,3,4-trifluophenyllithium and 4-propylcyclohexanone and subsequent dehydration with p-toluenesulfonic acid), 0.1 g of palladium-on-active charcoal (1%) and 15 ml of toluene is hydrogenated to saturation at room temperature. After filtration and removal of the solvent, the residue is dissolved in 15 ml of dimethyl sulfoxide, 1.2 g of potassium tert.-butanolate are added and the mixture is stirred at room temperature for 2 hours. Acidification and customary working up give trans-1-(2,3,4-trifluorophenyl)-4-propylcyclohexane.

The following compounds are prepared analogously:
trans-1-(2,3,4-trifluorophenyl)-4-ethylcyclohexane
trans-1-(2,3,4-trifluorophenyl)-4-butylcyclohexane
trans-1-(2,3,4-trifluorophenyl)-4-pentylcyclohexane
trans-1-(2,3,4-trifluorophenyl)-4-hexylcyclohexane
trans-1-(2,3,4-trifluorophenyl)-4-heptylcyclohexane
trans-1-(2,3,4-trifluorophenyl)-4-octycyclohexane
trans-1-(4-propyl-2,3-difluorophenyl)-4-ethylcyclohexane
trans-1-(4-propyl-2,3-difluorophenyl)-4-propylcyclohexane
trans-1-(4-propyl-2,3-difluorophenyl)-4-butylcyclohexane
trans-1-(4-propyl-2,3-difluorophenyl)-4-pentylcyclohexane
trans-1-(4-propyl-2,3-difluorophenyl)-4-hexylcyclohexane
trans-1-(4-propyl-2,3-difluorophenyl)4-heptylcyclohexane
trans-1-(4-propyl-2,3-difluorophenyl)-4-octylcyclohexane
trans-1-(4-pentyl-2,3-difluorophenyl)-4-ethylcyclohexane
trans-1-(4-pentyl-2,3-difluorophenyl)-4-propylcyclohexane
trans-1-(4-pentyl-2,3-difluorophenyl)-4-butylcyclohexane
trans-1-(4-pentyl-2,3-difluorophenyl)-4-pentylcyclohexane
trans-1-(4-pentyl-2,3-difluorophenyl)-4-hexylcyclohexane
trans-1-(4-pentyl-2,3-difluorophenyl)-4-heptylcyclohexane
trans-1-(4-pentyl-2,3-difluorophenyl)-4-octylcyclohexane
trans-1-(4-ethoxy-2,3-difluorophenyl)-4-ethylcyclohexane
trans-1-(4-ethoxy-2,3-difluorophenyl)-4-propylcyclohexane
trans-1-(4-ethoxy-2,5-difluorophenyl)-4-butylcyclohexane
trans-1-(4-ethoxy-2,3-difluorophenyl)-4-pentylcyclohexane
trans-1-(4-ethoxy-2,3-difluorophenyl)-4-hexylcyclohexane
trans-1-(4-ethoxy-2,3-difluorophenyl)-4-heptylcyclohexane
trans-1-(4-ethoxy-2,3-difluorophenyl)-4-octylcyclohexane
trans-1-(4-octyloxy-2,3-difluorophenyl)-4-ethylcyclohexane
trans-1-(4-octyloxy-2,3-difluorophenyl)4-propylcyclohexane
trans-1-(4-octyloxy-2,3-difluorophenyl)-4-butylcyclohexane
trans-1-(4-octyloxy-2,3-difluorophenyl)-4-pentylcyclohexane
trans-1-(4-octyloxy-2,3-difluorophenyl)-4-hexylcyclohexane
trans-1-(4-octyloxy-2,3-difluorophenyl)-4-heptylcyclohexane
trans-1-(4-octyloxy-2,3-difluorophenyl)-4-octylcyclohexane
trans-trans-4'-(4-pentyl-2,3-difluorophenyl)-4-ethylbicyclohexane trans-trans-4'-(4-pentyl-2,3-difluorophenyl)-4-propylbicyclohexane trans-trans-4'-(4-pentyl-2,3-difluorophenyl)-4-butylbicyclohexane trans-trans-4'-(4-pentyl-2,3-difluorophenyl)-4-pentylbicyclohexane trans-trans-4'-(4-pentyl-2,3-difluorophenyl)-4-hexylbicyclohexane trans-trans-4'-(4-pentyl-2,3-difluorophenyl)-4-heptylbicyclohexane trans-trans-4'-(4-pentyl-2,3-difluorophenyl)-4-octylbicyclohexane trans-trans-4'-(2,3-difluorophenyl)-4-ethylbicyclohexane trans-trans-4'-(2,3-difluorophenyl)-4-propylbicyclohexane C 41° S$_B$ 81° N96.4° I trans-trans-4'-(2,3-difluorophenyl)-4-butylbicyclohexane trans-trans-4'-(2,3-difluorophenyl)-4-pentylbicyclohexane trans-trans-4'-(2,3,-difluorophenyl)-4-hexylbicyclohexane trans-trans-4'-(2,3-difluorophenyl)-4-heptylbicyclohexane trans-trans-4'-(2,3-difluorophenyl)-4-octylbicyclohexane

Example 4 a) 4-Ethoxy-2,3-difluorobenzaldehyde 125 ml of a solution of 0.2 mol of n-butyllithium in hexane are added to a mixture of 0.2 mol of 2,3-difluorophenyl, 0.2 mol of tetramethylethylenediamine and 400 ml of tetrahydrofuran at −78° C. and the mixture is stirred at −60° C. for 2 hours. A mixture of 0.2 mol of N-formulpiperidine and 20 ml of tetrahydrofuran is added dropwise to this mixture. After warming to −20° C. and customary working up, the aldehyde is obtained as a colourless solid, mp. 70° C.

b) 4-Ethoxy-2,3-difluorobenzonitrile

A mixture of 0.12 mol of hydroxylamine-O-sulfonic acid and 50 ml of water is added to a mixture of 0.1 mol of 4-ethoxy-2,3-difluorobenzaldehyde and 100 ml of water at 30° C. and the mixture is stirred for 1 hour. After heating at 65° C. for 2 hours and customary working up, the nitrile is obtained as a colourless solid, mp. 45° C.

c) 2,3-Difluoro-4-cyanophenol

A mixture of 0.1 mol of 4-ethoxy-2,3-difluorobenzontrile, 0.12 mol of aluminum chloride and 150 ml of toluene is heated at the boiling point for 2 hours. Customary working up gives the phenol as a colourless solid, mp. 145° C.

Example 5

A mixture of 0.11 mol of dicyclohexylcarbodiimide and 20 ml of toluene is added to a mixture of 0.1 mol of p-pentylbenzoic acid, 0.1 mol of 2,3-difluoro-4-cyanophenol (prepared according to Example 4), 1.5 g of 4-N,N-dimethylaminopyridine and 200 ml of toluene. After the mixture has been stirred at room temperature for 4 hours, 0.4 g of oxalic acid is added and stirring is continued for a further 30 minutes. Customary working up gives 4-(4-pentylbenzoyloxy)-2,3-difluorobenzonitrile, mp. 33° C.

The following compounds are prepared analogously:

4-(4-ethylbenzoyloxy)-2,3-difluorobenzonitrile 4-(4-propylbenzoyloxy)-2,3-difluorobenzonitrile 4-(4-butylbenzoyloxy)-2,3-difluorobenzontrile 4-(4-hexylbenzoyloxy)-2,3-difluorobenzonitrile 4-(4-heptylbenzoyloxy)-2,3-difluorobenzonitrile 4-(4-octylbenzoyloxy)-2,3-difluorobenzontrile 4-(4-(trans-4-ethylcyclohexyl)-benzoyloxy)-2,3-difluorobenzonitrile 4-(4-(trans-4-propylcyclohexyl)-benzoyloxy)-2,3-difluorobenzonitrile, C 98° N 105.9° I 4-(4-(trans-4-butylcyclohexyl)-benzoyloxy)-2,3-difluorobenzonitrile 4-(4-(trans-4-pentylcyclohexyl)-benzoyloxy)-2,3-difluorobenzonitrile 4-(4-(trans-4-hexylcyclohexyl)-benzoyloxy)-2,3-difluorobenzonitrile 4-(4-(trans-4-heptylcyclohexyl)-benzoyloxy)-2,3-difluorobenzonitrile 4-(4-(trans-4-octylcyclohexyl)-benzoyloxy)-2,3-difluorobenzonitrile

Example 6

A mixture of 0.1 mol of trans-4-octylcyclohexanecarbonyl chloride (prepared from the carboxylic acid with oxalyl chloride in toluene) and 75 ml of methylene chloride is added to a mixture of 0.1 mol of 2,3-difluoro-4-cyanophenol (prepared according to Example 4), 0.12 mol of pyridine, 10 mmol of 4-N,N-dimethylaminopyridine and 250 ml of methylene chloride. After the mixture has been stirred at room temperature for 10 hours, it is washed with dilute hydrochloric acid, saturated sodium bicarbonate solution and water. Customary working up gives 4-(trans-4-octylcyclohexanecarbonyloxy)-2,3-difluorobenzonitrile.

Example 7 a) 1-(4-Pentylcyclohex-1-enyl)-2,3-difluorobenzene

A solution of 0.525 mol of n-butyllithium in 320 ml of hexane is added to a mixture of 0.5 mol of 1,2-difluorobenzene, 1,000 ml of tetrahydrofuran and 0.5 mol of tetramethylethylenediamine at −78° C. After the mixture has been stirred at −60° C. for 3 hours, 0.525 mol of 4-pentylcyclohexanone dissolved in 100 ml of tetrahydrofuran is added dropwise and the mixture is allowed to warm slowly to room temperature. The alcohol obtained after neutralization is dissolved, without purification, in 250 ml of toluene and heated with 2 g of p-toluene-sulfonic acid for 3 hours using a water separator. Customary working up gives 1-(4-pentylcyclohex-1-enyl)-2,3-difluorobenzene of boiling point 123° C./0.5 mm Hg.

b) 4-(4-Pentylcyclohex-1-enyl)-2,3-difluorobenzaldehyde 0.12 mol of N-formylpiperidine in 20 ml of tetrahydrofuran is added to 0.1 mol of 4-(4-pentycyclohex-1-enyl)- 2,3-difluorophenyllithium (prepared from the benzene with n-butyllithium in tetrahydrofuran/tetramethylethylenediamine analogously to Example 7a)) at −70° C. and the mixture is warmed to −20° C. in the course of 1 hour. Acidification and customary working up give the aldehyde.

c) 4-(4-Pentylcyclohex-1-enyl)-2,3-difluorobenzonitrile

A mixture of 0.12 mole of hydroxylamine-O-sulfonic acid and 50 ml of water is added to a mixture of 0.1 mol of the aldehyde and 100 ml of water at 30° C. After the mixture has been stirred at room temperature for 1 hour, it is heated at 65° C. for 2 hours. Cooling and customary working up give the nitrile as a white solid.

d) Oxidation with 2,3-dichloro-5,6-dicyanobenzoquinone (DDQ)

0.2 mol of DDQ is added to a mixture of 0.1 mol of the cyclohexene derivative from Example 7c) and 200 ml of toluene and the mixture is heated at the boiling point for 2 hours. Cooling and customary working up give 4-pentyl-4'-cyano-2',3'-difluorobiphenyl.

The following compounds are prepared analogously:
4-ethyl-4'-cyano-2',3'-difluorobiphenyl
4-propyl-4'-cyano-2',3'-difluorobiphenyl
4-butyl-4'-cyano-2',3'-difluorobiphenyl
4-hexyl-4'-cyano-2',3'-difluorobiphenyl
4-heptyl-4'-cyano-2',3'-difluorobiphenyl
4-octyl-4'-cyano-2',3'-difluorobiphenyl
4-(trans-4-ethylcyclohexyl)-4'-cyano-2',3'-difluorobiphenyl
4-(trans-4-propylcyclohexyl)-4'-cyano-2',3'-difluorobiphenyl
4-(trans-4-butylcyclohexyl)-4'-cyano-2',3'-difluorobiphenyl
4-(trans-4-pentylcyclohexyl)-4'-cyano-2',3'-difluorobiphenyl, C 84° N 168° I
4-(trans-4-hexylcyclohexyl)-4'-cyano-2',3'-difluorobiphenyl
4-(trans-4-heptylcyclohexyl)-4'-cyano-2',3'-difluoro biphenyl
4-(trans-4-octylcyclohexyl)-4'-cyano-2',3'-difluorobiphenyl

Example 8 a) 1-(2,3-Difluoropheny)-2-(trans-4-pentylcyclohexyl)-ethane

A solution of 0.21 mol of n-butyllithium in 130 ml of hexane is added to a mixture of 0.25 mol of 1,2-difluorobenzene, 0.20 mol of potassium tert.-butanolate and 200 ml of tetrahydrofuran at −100° C. After the mixture has been stirred for 10 minutes, a mixture of 0.2 mol of 2-(trans-4-pentylcyclohexyl)-ethyl iodide, 0.2 mol of dimethylaminepropyleneurea and 50 ml of tetrahydrofuran is added at −90° C. After the mixture has been stirred at −40° C. for 1 hour, customary working up gives the ethane derivative of boiling point 135° C./0.5 mm Hg, in addition to a little 1,4-di-(2-trans-4-pentylcyclohexyl)-ethyl)-2,3-difluorobenzene as a by-product, of C 64° C. N 106.7° I.

b) 4-(2-(Trans-4-pentylcyclohexyl)-ethyl)-2,3-difluorobenzonitrile 0.1 mol of the ethane derivative are deprotonated in accordance with Example 7a), formylated in accordance with Example 7b) and reacted with 0.12 mol of hydroxylamine-O-sulfonic acid in accordance with Example 7c). Customary working up gives the nitrile as a colourless solid, C 13° N 28.5° I.

Example 9

0.1 mol of 2,3-difluoro-4-ethoxyphenol (which can be prepared from 2,3-difluorophenol by alkylation with diethyl sulfate/potassium carbonate in dimethylformamide, lithiation at −70° to −80°, reaction with N-methylpipidine and oxidation of the aldehyde by the Baeyer-Villiger method with performic acid) and 0.1 mol of pyridine are dissolved in 100 ml of toluene. 0.1 mol of trans-4-pentylcyclohexanecarbonyl chloride is added dropwise at 80° and the mixture is subsequently stirred for 3 hours. The pyridine hydrochloride which has precipitated is filtered off with suction, the toluene is distilled off and the 2,3-difluoro-4-ethoxyphenyl trans-4-pentylcyclohexanoate which remains is purified by crystallization from ethanol, C 48° N 62.5° I.

The following compounds are prepared analogously:
2,3-difluoro-4-ethoxyphenyl trans-4-propylcyclohexanoate, mp. 50° C. 52°
2,3-difluoro-4-propoxyphenyl trans-4-propylcyclohexanoate
2,3-difluoro-4-butoxyphenyl trans-4-propylcyclohexanoate
2,3-difluoro-4-pentyloxyphenyl trans-4-propylcyclohexanoate
2,3-difluoro-4-hexyloxyphenyl trans-4-propylcyclohexanoate
2,3-difluoro-4-heptyloxyphenyl trans-4-propylcyclohexanoate
2,3-difluoro-4-octyloxyphenyl trans-4-propylcyclohexanoate
2,3-difluoro-4-propoxyphenyl trans-4-pentylcyclohexanoate
2,3-difluoro-4-butoxyphenyl trans-4-pentylcyclohexanoate
2,3-difluoro-4-pentyloxyphenyl trans-4-pentylcyclohexanoate
2,3-difluoro-4-hexyloxyphenyl trans-4-pentylcyclohexanoate
2,3-difluoro-4-heptyloxyphenyl trans-4-pentylcyclohexanoate
2,3-difluoro-4-octyloxyphenyl trans-4-pentylcyclohexanoate

Example 10

2,3-Difluoro-4-ethoxyphenyl trans-4-(trans-4-propylcyclohexyl)-cyclohexanoate is obtained analogously to Example 9 from the same phenol by reaction with 4-(trans-4-propylcyclohexyl)-cyclohexanecarbonyl chloride, C 69.3° $S_C$ 146.9° $S_A$ 152.7° N 156° I.

The following compounds are prepared analogously:
2,3-difluoro-4-propoxyphenyl trans-4-(trans-4-propylcyclohexyl)-cyclohexanoate
2,3-difluoro-4-butoxyphenyl trans-4-(trans-4-propylcyclohexyl)-cyclohexanoate
2,3-difluoro-4-pentyloxyphenyl trans-4-(trans-4-propylcyclohexyl)-cyclohexanoate
2,3-difluoro-4-hexyloxyphenyl trans-4-(trans-4-propylcyclohexyl)-cyclohexanoate
2,3-difluoro-4-heptyloxyphenyl trans-4-trans-4-propylcyclohexyl)-cyclohexanoate
2,3-difluoro-4-octyloxyphenyl trans-4-(trans-4-propylcyclohexyl)-cyclohexanoate
2,3-difluoro-4-ethylphenyl trans-4(trans-4-propylcyclohexyl)-cyclohexanoate
2,3-difluoro-4-propylophenyl trans-4-(trans-4-propylcyclohexyl)-cyclohexanoate
2,3-difluoro-4-butylphenyl trans-4-(trans-4-propylcyclohexyl)-cyclohexanoate
2,3-difluoro-4-pentylphenyl trans-4-(trans-4-propylcyclohexyl)-cyclohexanoate, C 50° $S_B$ 98° $S_A$ 115° N 178.7° I.
2,3-difluoro-4-hexylphenyl trans-4(trans-4-propylcyclohexyl)-cyclohexanoate 2,3-difluoro-4-heptylphenyl trans-4-(trans-4-propylcyclohexyl)-cyclohexanoate
2,3-difluoro-4-octylphenyl trans-4-(trans-4-propylcyclohexyl)-cyclohexanoate
2,3-difluoro-4-ethoxyphenyl trans-4butylcyclohexanoate, C 49° N (48.2°) I
2,3-difluoro-4-octyloxyphenyl trans-4-pentylcyclohexanoate, C 59° S$_A$ (55°) I
2,3-difluoro-4-octyloxyphenyl trans-4-heptylcyclohexanoate, C 53° N 65.7° I
2,3-difluoro-4-ethoxyphenyl trans-4-(trans-4-butylcyclohexyl)-cyclohexanoate
2,3-difluoro-4-ethoxyphenyl trans-4-(trans-4-pentylcyclohexyl)-cyclohexanoate
2,3-difluoro-4-ethoxyphenyl trans-4-(trans-4-hexylcyclohexyl)-cyclohexanoate
2,3-difluoro-4-ethoxyphenyl trans-4-(trans-4-heptylcyclohexyl)-cyclohexanoate
2,3-difluoro-4-ethoxyphenyl trans-4-(trans-4-octylcyclohexyl)-cyclohexanoate

Example 11

0.1 mol of 4-hexyloxybenzoic acid, 0.01 mol of dimethylaminopyridine and 0.1 mol of 2,3-difluoro-4-octyloxyphenol (which can be prepared from 2,3-difluorooctyloxybenzene by lithiation at −70° to −80° and dropwise addition of a solution, prepared from 0.12 mol of t-butyl hydroperoxide and 0.12 mol of butyllithium, of lithium t-butyl peroxide in ether) are initially introduced into 150 ml of methylene chloride, a solution of 0.1 mol of dicyclohexylcarbodiimide in 30 ml of methylene chloride is added dropwise at 10°, while stirring, and the mixture is then subsequently stirred at room temperature for 15 hours. The mixture is filtered over silica gel and the solvent is evaporated off the give 2,3-difluoro-4-octyloxyphenyl 4-hexyloxybenzoate as the residue.

The following compounds are prepared analogously:
2,3-difluoro-4-octyloxyphenyl p-(4-heptyloxy-3-fluorophenyl)-benzoate, C 69.3° S$_C$ 146.9° S$_A$ 152.7° N 156° I
2,3-difluoro-4-octyloxyphenyl p-(4-octyloxy-3-fluorophenyl)-benzoate
2,3-difluoro-4-octyloxyphenyl p-(4-nonyloxy-3-fluorophenyl)-benzoate, C 71.7° S$_C$ 146° S$_A$ 149.8° N 150.2° I
2,3-difluoro-4-octyloxyphenyl p-(4-decyloxy-3-fluorophenyl)-benzoate
2,3-difluoro-4-nonyloxyphenyl p-(4-heptyloxy-3-fluorophenyl)-benzoate
2,3-difluoro-4-nonyloxyphenyl p-(4-octyloxy-3-fluorophenyl)-benzoate
2,3-difluoro-4-nonyloxyphenyl p-(4-nonyloxy-3-fluorophenyl)-benzoate
2,3-difluoro-4-nonyloxyphenyl p-(4-decyloxy-3-fluorophenyl)-benzoate
2,3-difluoro-4-decyloxyphenyl p-(4-hept oxy-3-fluorophenyl)-benzoate
2,3-difluoro-4-decyloxyphenyl p-(4-octyloxy-3-fluorophenyl)-benzoate
2,3-difluoro-4-decyloxyphenyl p-(4-nonyloxy-3-fluorophenyl)-benzoate
2,3-difluoro-4-decyloxyphenyl p-(4-decyloxy-3-fluorophenyl)-benzoate
4-heptyloxy-2,3-difluorophenyl p-hexylbenzoate
4-heptyloxy-2,3-difluorophenyl p-heptylbenzoate
4-heptyloxy-2,3-difluorophenyl p-octylbenzoate, mp. 43.5°
4-heptyloxy-2,3-difluorophenyl p-nonylbenzoate
4-heptyloxy-2,3-difluorophenyl p-decylbenzoate
4-heptyloxy-2,3-difluorophenyl p-hexyloxybenzoate
4-heptyloxy-2,3-difluorophenyl p-heptyloxybenzoate
4-heptyloxy-2,3-difluorophenyl p-octyloxybenzoate, C 53° (S$_C$ 39°) N 57° I
2,3-difluoro-4-heptyloxyphenyl p-(4-hexyl-3-fluorophenyl)-benzoate
2,3-difluoro-4-heptyloxyphenyl p-(4-heptyl-3-fluorophenyl)-benzoate
2,3-difluoro-4-heptyloxyphenyl p-(4-octyl-3-fluorophenyl)-benzoate, C 60° S$_C$ 150° S$_A$ 155° N 157° I
2,3-difluoro-4-heptyloxyphenyl p-(4-hexylphenyl)-benzoate
2,3-difluoro-4-heptyloxyphenyl p-(4-heptylphenyl)-benzoate
2,3-difluoro-4-heptyloxyphenyl p-(4-octylphenyl)-benzoate, C 86° S$_c$ 125° S$_A$ 131° N 145° I
2,3-difluoro-4-heptyloxyphenyl p-(4-hexyloxyphenyl)-benzoate
2,3-difluoro-4-heptyloxyphenyl p-(4-heptyloxyphenyl)-benzoate
2,3-difluoro-4-heptyloxyphenyl p-(4-octyloxyphenyl)-benzoate, C 94° S$_c$ 157° S$_A$ 166° N 174° I
4-octyloxy-2,3-difluorophenyl p-hexylbenzoate
4-octyloxy-2,3-difluorophenyl p-heptylbenzoate
4-octyloxy-2,3-difluorophenyl p-octylbenzoate
4-octyloxy-2,3-difluorophenyl p-nonylbenzoate
4-octyloxy-2,3-difluorophenyl p-hexyloxybenzoate
4-octyloxy-2,3-difluorophenyl p-heptyloxybenzoate
4-octyloxy-2,3-difluorophenyl p-octyloxybenzoate, C 51° S$_C$ (39°) N 59.8° I
4-octyloxy-2,3-difluorophenyl p-nonyloxybenzoate, C 53.6° S$_C$ (49°) N 59.3° I
4-octyloxy-2,3-difluorophenyl trans-4-pentylcyclohexylcarboxylate, C 30° N 60° I
4-octyloxy-2,3-difluorophenyl trans,trans-4'-pentylbicyclohexyl-4-carboxylate, C 58° S$_C$ (38°) S$_A$ 167° N 182.5° I
4-octyloxy-2,3-difluorophenyl 4-(trans-4-pentylcyclohexyl)-benzoate, C 62° S$_C$ 63° S$_A$ 100° N 152.2° I
4-heptyloxy-2,3-difluorophenyl p-octyloxybenzoate, C 53° N 57° I
4-heptyloxy-2,3-difluorophenyl p-octylbenzoate, C 43.5° I

Example 12

0.1 mol of 2,3-difluoro-4-butoxyphenol, 0.11 mol of trans-4-pentylcyclohexylmethyl bromide and 0.11 mol of potassium carbonate are heated at 100° in 100 ml of dimethylformamide (DMF) for 16 hours. After cooling, the inorganic salts are filtered off with suction, the filtrate is concentrated and water is added. Extraction with methylene chloride gives 1-butoxy-2,3-difluoro-4-(trans-4-pentylcyclohexylmethoxy)benzene.

The following compounds are prepared analogously:
1-ethoxy-2,3-difluoro-4-(trans-4-pentylcyclohexylmethoxy)-benzene, C 38° I
1-propoxy-2,3-difluoro-4-(trans-4-pentylcyclohexylmethoxy)-benzene
1-pentyloxy-2,3-difluoro-4-(trans-4-pentylcyclohexylmethoxy)-benzene
1-hexyloxy-2,3-difluoro-4-(trans-4-pentylcyclohexylmethoxy)-benzene
1-heptyloxy-2,3-difluoro-4-(trans-4-pentylcyclohexylmethoxy)-benzene
1-octyloxy-2,3-difluoro-4-(trans-4-pentylcyclohexylmethoxy)-benzene 1-ethyl-2,3-difluoro-4-(trans-4-pentylcyclohexylmethoxy)-benzene
1-propyl-2,3-difluoro-4-(trans-4-pentylcyclohexylmethoxy)-benzene
1-butyl-2,3-difluoro-4-(trans-4-pentylcyclohexylmethoxy)-benzene
1-pentyl-2,3-difluoro-4-(trans-4-pentylcyclohexylmethoxy)-benzene
1-hexyl-2,3-difluoro-4-(trans-4-pentylcyclohexylmethoxy)-benzene
1-heptyl-2,3-difluoro-4-(trans-4-pentylcyclohexylmethoxy)-benzene
1-octyl-2,3-difluoro-4-(trans-4-pentylcyclohexylmethoxy)-benzene
1-ethyl-2,3-difluoro-4-(trans,trans-4'-propylbicyclohexyl-4-ylmethoxy)-benzene
1-propyl-2,3-difluoro-4-(trans,trans-4'-propylbicyclohexyl-4-ylmethoxy)-benzene
1-butyl-2,3-difluoro-4-(trans,trans-4'-propylbicyclohexyl-4-ylmethoxy)-benzene
1-pentyl-2,3-difluoro-4-(trans,trans-4'-propylbicyclohexyl-4-ylmethoxy)-benzene, C 36° $S_A$ 66° N 117.1° I
1-hexyl-2,3-difluoro-4-(trans,trans-4'-propylbicyclohexyl-4-ylmethoxy)-benzene
1-heptyl-2,3-difluoro-4-(trans,trans-4'-propylbicyclohexyl-4-ylmethoxy)-benzene
1-octyl-2,3-difluoro-4-(trans,trans-4'-propylbicyclohexyl-4-ylmethoxy)-benzene
1,2,3-trifluoro-4-(trans-4-(trans-4-propylcyclohexyl)-cyclohexylmethoxy)-benzene, C 68° N 105.2° I
1,2,3-trifluoro-4-(trans-4-(trans-4-ethylcyclohexyl)-cyclohexylmethoxy)-benzene
1,2,3-trifluoro-4-(trans-4-(trans-4-butylcyclohexyl)-cyclohexylmethoxy)-benzene
1,2,3-trifluoro-4-(trans-4-(trans-4-pentylcyclohexyl)-cyclohexylmethoxy)-benzene, C 81° N 111.5° I
1,2,3-trifluoro-4-(trans-4-(trans-4-hexylcyclohexyl)-cyclohexylmethoxy)-benzene
1,2,3-trifluoro-4-(trans-4-(trans-4-heptylcyclohexyl)-cyclohexylmethoxy)-benzene
1,2,3-trifluoro-4-(trans-4-(trans-4-octylcyclohexyl)-cyclohexylmethoxy)-benzene

Example 13

0.05 mol of 2,3-difluorohydroquinone and 0.1 mol of pyridine are dissolved in 100 ml of toluene. 0.1 mol of trans-4-butylcyclohexanecarbonyl chloride is added dropwise at 80° and the mixture is subsequently stirred for 3 hours. Customary working up gives 2,3-difluoro-1,4-bis-(trans-4-butylcyclohexanoyloxy)-benzene.

The following compounds are prepared analogously:
2,3-difluoro-1,4-bis-(trans-4-ethylcyclohexanoyloxy)-benzene
2,3-difluoro-1,4-bis-(trans-4-propylcyclohexanoyloxy)-benzene
2,3-difluoro-1,4-bis-(trans-4-pentylcyclohexanoyloxy)-benzene, C 87° N 208° I
2,3-difluoro-1,4-bis-(trans-4-hexylcyclohexanoyloxy)-benzene
2,3-difluoro-1,4-bis-(trans-4-heptylcyclohexanoyloxy)-benzene
2,3-difluoro-1,4-bis-(trans-4-octylcyclohexanoyloxy)-benzene, C 80° $S_C$ 123° N 177° I

Example 14

0.1 mol of 2,3-difluoro-4-ethoxybenzoic acid (which can be prepared from 2,3-difluorophenol by alkylation with diethyl sulfate/potassium carbonate in dimethylformamide, metalation of the 2,3-difluorophenetol in the 4-position with butyllithium/tetramethylethylenediamine in tetrahydrofuran at −70 to −80° and reaction with solid carbonic acid), 0.01 mol of 4-dimethylaminopyridine and 0.1 mol of 2-pentyl-5-hydroxypyridine are initially introduced into 150 ml of methylene chloride, a solution of 0.1 mol of dicyclohexylcarbodiimide in 30 ml of methylene chloride is added dropwise at 10°, while stirring, and the mixture is then subsequently stirred at room temperature for 15 hours. The mixture is filtered with suction over silica gel to give, after customary working up, 5-(2-pentylpyridyl) 2,3-difluoro-4-ethoxybenzoate.

The following compounds are prepared analogously:
2-(5-octylpyridyl) 2,3-difluoro-4-heptyloxybenzoate
2-(5-nonylpyrimidyl)2,3-difluoro-4-nonyloxybenzoate
2-(5-(2-(trans-4-heptylcyclohexyl)-ethyl)-pyrimidyl)2,3-difluoro-4-octyloxybenzoate, C 73° $S_C$ 115° N 134° I

Example 15

Lithiation of o-difluorobenzene at −70° to −80° and reaction with propionaldehyde, dehydration of the secondary alcohol formed and subsequent hydrogenation of the double bond gives 2,3-difluoropropylbenzene. Renewed metalation and reaction with dry ice gives 2,3-difluoro-4-propylbenzoic acid. 4-(5-Heptylpyrimidin-2-yl)-phenyl 2,3-difluoro-4-propylbenzoate is obtained from this acid analogously to Example 1 by esterification with 2-(4-hydroxyphenyl)-5-heptylpyrimidine and dicyclohexylcarbodiimide, C 69° N 138° I.

The following compound is prepared analogously:
4-(5-heptylpyrimidin-2-yl)-phenyl 2,3-difluoro-4-octyloxybenzoate

Example 16

0.1 mol of 2,3-difluoro-4-ethoxybenzoic acid (which can be prepared from 2,3-difluorophenol by alkylation with diethyl sulfate/potassium carbonate in dimethylformamide, metalation of the 2,3-difluorophenetol in the 4-position using butyllithium/tetramethylethylenediamine in tetrahydrofuran at −70° to −80° and reaction with solid carbonic acid), 0.01 mol of 4-diemthylaminopyridine and 0.1 mol of 4-hydroxy-4'-pentylbiphenyl are initially introduced into 150 ml of methylene chloride, a solution of 0.1 mol of dicyclohexylcarbodiimide in 30 ml of methylene chloride is added dropwise at 10°, while stirring, and the mixture is then subsequently stirred at room temperature for 15 hours. It is filtered with suction over silica gel and the solvent is evaporated to give 4-(4'-pentylbiphenylyl) 2,3-difluoro-4-ethoxybenzoate as the residue, which is purified by crystallization, C 94°, N 206.6° I.

The following compounds are prepared analogously:
trans-4hexylcyclohexyl 2,3-difluoro-4-(2-(trans-4-pentylcyclohexyl)-ethyl)-benzoate, C 49° $S_A$ 55° N 118° I
4-pentylphenyl 2,3-difluoro-4-(2-(trans-4-pentylcyclohexyl)-ethyl)-benzoate, C 45° $S_A$ 92° N 130.3 I
4-propylphenyl 2,3-difluoro-4-(4-pentylcyclohex-1-enyl)-benzoate, C 31° $S_A$ 63° N 150.8° I

Example 17

4-Pentylphenyl 2,3-difluoro-4-ethoxybenzoate is obtained analogously to Example 16 by reaction of 2,3-difluoro-4ethoxybenzoic acid with 4-pentylphenol, C 61°, N (50.7°) I.

The following compounds are prepared analogously:

p-octylphenyl 4-octyloxy-2,3-difluorobenzoate, C 37 S$_C$ 50 N 57.1 I 4-(trans-4-pentylcyclohexyl) 4-octyloxy-2,3-difluorobenzoate, C 58 S$_C$ 96 N 160.8 I trans,trans-4'-pentylbicyclohex-4-yl 4-octyloxy-2,3-difluorobenzoate, C 90 S$_C$ 98 N 170.3 I 4-(trans-4ethylcyclohexyl)-phenyl 4-propyl-2,3-difluorobenzoate, C 70 N 134.9 I trans,trans-4'-propylbicyclohexyl-4-yl 4-propyl-2,3-difluorobenzoate, C 64 N 165.2 I (4'-pentylbiphenyl-4-yl) 4-propyl-2,3-difluorobenzoate, C 74 S$_C$ 86 N 160.1 I (trans-4propylcyclohexyl) 4-ethoxy-2,3-difluorobenzoate, C 93 N (48) I

Example 18

4-(2,3-Difluoro-4'-propylbiphenylyl) 2,3-difluoro-4-pentylbenzoate is obtained analogously. The 4-hydroxy-2,3-difluoro-4'-propylbiphenyl needed for this is prepared as follows:

2,3-Difluoro-4'-propylbiphenyl is obtained by lithiation of o-difluorobenzene at −70° to −80°, reaction with 4-propylcyclohexanone, dehydration of the tertiary alcohol and subsequent aromatization of the cyclohexene ring. Renewed metalation and reaction with N-formylpiperidine gives 2,3-difluoro-4'-propylbiphenyl-4-carbaldehyde. The aldehyde is oxidized with 3-chloroperbenzoic acid in methylene chloride in accordance with the Bayer-Villiger method to give the formate, which is then hydrolyzed under alkaline conditions to give the desired phenol.

Example 19

2,3-Difluorooctylbenzene is obtained by lithiation of o-difluorobenzene at −70° to −80°, reaction with octanal, dehydration and hydrogenation. Renewed metalation and reaction with N-formylpiperidine to give the aldehyde, oxidation thereof by the Bayer-Villiger method to give the formate and subsequent hydrolysis gives 4-octyl-2,3-difluorophenol.

0.1 mol of the phenol and 0.1 mol of pyridine are dissolved in 100 ml of toluene. 0.1 mol of 4-hexyloxybenzoyl chloride, dissolved in 50 ml of toluene, is added dropwise at 80° and the mixture is subsequently stirred for 3 hours. The pyridine hydrochloride which has precipitated is filtered off with suction, the toluene is distilled off and the 2,3-difluoro-4-octylphenyl 4-hexyloxybenzoate which remains is purified by crystallization.

The following compounds are prepared analogously:
2,3-difluoro-4-octylphenyl 4-octyloxybenzoate
2,3-difluoro-4-decylphenyl 4-octyloxybenzoate
2,3-difluoro-4-pentylphenyl 4-ethoxybenzoate, C 42° N (26°) I
2,3-difluoro-4-pentylphenyl 4-propoxybenzoate
2,3-difluoro-4-pentylphenyl 4-butoxybenzoate
2,3-difluoro-4-pentylphenyl 4-pentyloxybenzoate
2,3-difluoro-4-pentylphenyl 4octyloxybenzoate

Example 20

0.1 mol of 2-fluoro-4-butyloxybenzoic acid (prepared from 3-fluoro-4-cyanophenol by alkylation with butyl bromide/potassium carbonate in dimethylformamide and subsequent hydrolysis of the nitrile via the imido ester), 0.01 mol of dimethylaminopyridine and 0.1 mol of 2,3-difluoro-4-octylphenol are initially introduced into 150 ml of methylene chloride, a solution of 0.1 mol of dicyclohexylcarbodiimide in 30 ml of methylene chloride is added dropwise at 10°, while stirring, and the mixture is then subsequently stirred at room temperature for 15 hours. The mixture is filtered over silica gel and the solvent is evaporated to give 2,3-difluoro-4-octylphenyl 2-fluoro-4-butyloxybenzoate as the residue.

Example 21

2,3-Difluorooctylbenzene is obtained by lithiation of o-difluorobenzene and reaction with octanal, dehydration and hydrogenation, and 4-octyl-2,3-difluorophenol is obtained therefrom via the formyl compound in accordance with Example 19.

0.1 mol of this phenol, 0.1 mol of trans-4-butylcyclohexanecarboxylic acid and 0.01 mol of 4-dimethylaminopyridine are initially introduced into 150 ml of methylene chloride, a solution of 0.1 mol of dicyclohexylcarbodiimide in 30 ml of methylene chloride is added dropwise at 10°, while stirring, and the mixture is then subsequently stirred at room temperature for 15 hours. The mixture is filtered over silica gel with suction and the solvent is evaporated off to give 2,3-difluoro-4-octylphenyl trans-4-butylcyclohexanoate as the residue.

Example 22

Analogously to Example 20, 2,3-difluoro-4-pentylphenol is obtained and is esterified with trans-4-(trans-4-pentylcyclohexyl)-cyclohexanecarboxylic acid. Customary working up gives 2,3-difluoro-4-pentylphenyl trans-4-(trans-4-pentylcyclohexyl)-cyclohexylcarboxylate, C 13° N 28.5° I.

The following compounds are prepared analogously:
2,3-difluoro-4-pentylphenyl trans-4-ethylcyclohexylcarboxylate
2,3-difluoro-4-pentylphenyl trans-4-propylcyclohexylcarboxylate
2,3-difluoro-4-pentylphenyl trans-4-butylcyclohexylcarboxylate
2,3-difluoro-4-pentylphenyl trans-4-hexylcyclohexylcarboxylate
2,3-difluoro-4-pentylphenyl trans-4-heptylcyclohexylcarboxylate
2,3-difluoro-4-pentylphenyl trans-4-octylcyclohexylcarboxylate
2,3-difluoro-4-entylphenyl trans-trans-4'-ethylbicyclohexyl-4-carboxylate
2,3-difluoro-4-pentylphenyl trans-trans-4'-propylbicyclohexyl-4-carboxylate
2,3-difluoro-4-pentylphenyl trans-trans-4'-butylbicyclohexyl-4-carboxylate
2,3-difluoro-4-pentylphenyl trans-trans-4'-pentylbicyclohexyl-4-carboxylate, S$_A$ 115° N 180° I
2,3-difluoro-4-pentylphenyl trans-trans-4'-hexylbicyclohexyl-4-carboxylate
2,3-difluoro-4-pentylphenyl trans-trans-4'-heptylbicyclohexyl-4-carboxylate
2,3-difluoro-4-pentylphenyl trans-trans-4'-octylbicyclohexyl-4-carboxylate
2,3-difluoro-4-pentylphenyl trans-4-(trans-4-ethylcyclohexyl)-benzoate
2,3-difluoro-4-pentylphenyl 4-(trans-4-propylcyclohexyl)-benzoate
2,3-difluoro-4-pentylphenyl 4-(trans-4-butylcyclohexyl)-benzoate
2,3-difluoro-4-pentylphenyl 4-(trans-4-pentylcyclohexyl)-benzoate, C 74° N 147° I
2,3-difluoro-4-pentylphenyl 4-(trans-4-hexylcyclohexyl)-benzoate 2,3-difluoro-4-pentylphenyl 4-(trans-4-heptylcyclohexyl)-benzoate 2,3-difluoro-4-pentylphenyl 4-(trans-4-octylcyclohexyl)-benzoate

Example 23

10 ml of a 20% solution of diisobutylaluminium hydride in hexane are added to a solution of 0.01 mol of 1-hexyne and 5 ml of hexane and the mixture is heated at 50° for 3 hours. It is then cooled to 25°, 6.3 ml of a 15% solution of butyllithium in hexane are added dropwise, after 30 minutes 0.01 mol of 2,3-difluoro-4-(trans-4-pentylcyclohexyl)-methoxybenzyl bromide, dissolved in 15 ml of tetrahydrofuran, are added dropwise and the mixture is heated under reflux for 12 hours. Working up gives 2,3-difluoro-4-(trans-4-pentylcyclohexyl)-methoxy-trans-hept-2-enylbenzene.

The benzyl bromide required is prepared from 2,3-difluoro-(trans-4-pentylcyclohexyl)-methoxybenzene by lithiation, reaction with N-formylpiperidine, reduction of the aldehyde with sodium borohydride and reaction of the benzyl alcohol with dibromotriphenylphosphorane.

Example 24

0.2 mol of 1-(4-ethoxy-2,3-difluorophenyl)-4-(trans-4-n-propylcyclohexylethyl)-cyclohex-1-ene (obtainable as follows: 131 ml of a 1.6N solution of butyllithium in n-hexane are added dropwise to a solution of 0.2 mol of ethoxy-2,3-difluorobenzene and 0.2 mol of tetramethylethylenediamine in 400 ml of tetrahydrofuran at −70° C., with exclusion of moisture and under a nitrogen atmosphere. The mixture is then stirred at −70° C. for 4 hours and 0.11 mol of 4-(trans-4-n-propylcyclohexylethyl)-cyclohexanone in 100 ml of THF are subsequently slowly added. The reaction mixture is allowed to warm slowly to room temperature and is hydrolysed with 1.5 l of a saturated ammonium chloride solution. The mixture is extracted with ether and the ether phase is washed several times with water, dried and evaporated. The residue is taken up in 700 ml of ethanol, 70 ml of concentrated HCl are added and the mixture is boiled under reflux for 3 hours. 1.5 l of water are then added and the mixture is extracted with methyl tert.-butyl ether. The ether phase is washed neutral, dried and evaporated and the residue is recrystallized. The product (has a mp. of 73° and a cp. of 139°) and 50 g of DDQ are boiled under reflux in 250 ml of toluene for one hour. After cooling, the reaction mixture is filtered with toluene over silica gel, the filtrate is evaporated and the residue is purified by chromatography. 1-(trans-4-Propylcyclohexyl)-2-(4'-ethoxy-2',3'-difluorobiphenyl-4-yl)-ethane is obtained, C 64° N 144° I.

Example 25

125 ml of a 1.6N solution of n-BuLi in hexane are added dropwise to a solution of 0.2 mol of trans-4-n-propylcyclohexylethyl-2,3-difluorobenzene (which can be prepared by alkylation of 2,3-difluorobenzene with trans-4-n-propylcyclohexylethyl iodide at −85° C. in the presence of BuLi/potassium tert.-butylate (t-BuOK)/1,3-dimethyltetrahydro-2(1H)-pyrimidinone (DMPU) and 0.2 mol of TMEDA in 400 ml of THF at −70° C.), with exclusion of moisture and under a nitrogen atmosphere. The mixture is stirred at −70° for 4 hours and 0.2 mol of 4-pentyloxycyclohexanone are then added. The reaction mixture is allowed to warm to room temperature and is then hydrolysed with dilute HCl, and the product is isolated in the customary manner. The product is taken up in toluene and the mixture is heated at the boil in the presence of p-toluenesulfonic acid, using a water separator. The toluene phase is then washed neutral with water and dried and 0.4 mmol of DDQ are added. The reaction mixture is brought to the boil. When the reaction has ended, the mixture is filtered over a silica gel column and is then worked up in the customary manner. The product is purified by crystallization and chromatography. 1-(trans-4-Propyl)-cyclohexyl)-2-(4'-pentyloxy-2,3-difluorobiphenyl-4-yl)-ethane is obtained.

The following compounds are prepared analogously:

1-(trans-4-ethylcyclohexyl)-2-(4'-pentyloxy-2,3-difluorobiphenyl-4-yl)-ethane 1-(trans-4-butylcyclohexyl)-2-(4'-pentyloxy-2,3-difluorobiphenyl-4-yl)-ethane 1-(trans-4-pentylcyclohexyl)-2-(4'-pentyloxy-2,3-difluorobiphenyl-4-yl)-ethane 1-(trans-4-hexylcyclohexyl)-2-(4'-pentyloxy-2,3-difluorobiphenyl-4-yl)-ethane 1-(trans-4-heptylcyclohexyl)-2-(4'-pentyloxy-2,3-difluorobiphenyll-4-yl)-ethane biphenyl-4-yl)-ethane 1-(trans-4-octylcyclohexyl)-2-(4'-pentyloxy-2,3-difluorobiphenyl-4-yl)-ethane 1-(trans-4-ethylcyclohexyl)-2-(4-ethoxy-2,3-dfluorophenyl)-ethane 1-(trans-4-propylcyclohexyl)-2-(4-ethoxy-2,3-difluorophenyl)-ethane 1-(trans-4-butylcyclohexyl)-2-(4-ethoxy-2,3-difluorophenyl)-ethane 1-(trans-4-pentylcyclohexyl)-2-(4-ethoxy-2,3-difluorophenyl)-ethane, C 49° N (20°) I 1-(trans-4-pentylcyclohexyl)-2-(4-hexanoyloxy-2,3-difluorophenyl)-ethane, C 45° N (26.4°) I 1-(trans-4-pentylcyclohexyl)-2-(4-(trans-4-pentylcyclohexylcarbonyloxy)-2,3-difluorophenyl)-ethane, C 58° N 151.8° I 1-(trans-4-pentylcyclohexyl)-2-(4-(4-octyloxybenzoyloxy)-2,3-difluorophenyl)-ethane, C 51° N 138° I 1-(trans-4-pentylcyclohexyl)-2-(4-(trans-4-pentylcyclohexylmethoxy)-2,3-difluorophenyl)-ethane, C 76 $S_A$ (72°) N 109.4° I 1-(trans-4-pentylcyclohexyl)-2-(4'-pentyl-2,3-difluorobiphenyl-4-yl)-ethane, C 22° N 106.7° I 1-(4-(trans-4pentylcyclohexyl)-phenyl)-2-(4-ethoxy-2,3-difluorophenyl)-ethane, C 49° $S_B$ (31°) N 107.3° I 1-(4-(trans-4-propylcyclohexyl)-phenyl)-2-(4-ethoxy-2,3-difluorophenyl)-ethane, C 75° N 99.5° I

Example 26

0.1 mol of dicyclohexylcarbodiimide (DCC) dissolved in $CH_2Cl_2$ is added to 0.1 mol of 4'-pentyl-2,3-difluorobiphenyl-4-ol (which can be prepared from 4'-pentyl-2,3-difluoro-4-methoxy-biphenyl by ether cleavage with HBr/glacial acetic acid), 0.1 mol of trans-4-n-pentyl-cyclohexanecarboxylic acid and a catalytic amount of 4-N,N'-dimethylaminopyridine (DMAP) in 300 ml of $CH_2Cl_2$ at 0° C., with exclusion of moisture. The mixture is then stirred at room temperature for 12 hours, the dicyclohexylurea which has precipitated is separated off and the product is worked up in the customary manner. The product is purified by crystallization. 4'-Pentyl-2,3-difluorobiphenyl-4-yl trans-4-n-Pentylcyclohexanecarboxylate is obtained, C 44° N 159.1° I.

Example 27

0.1 mol of 4'-n-pentyl-2,3-difluorobiphenyl-4-ol and 0.1 mol of trans-4-n-pentylcyclohexylmethyl iodide and heated in the presence of 0.12 mol of anhydrous $K_2CO_3$ in dimethylformamide (DMF) until the mixture boils gently. When the reaction has ended, the mixture is worked up in the customary manner and the product is purified by chromatography and crystallization. Trans-4-n-pentylcyclohexylmethyl 4'-pentyl-2,3-difluorobiphenyl-4-yl ether is obtained.

Example 28

13.6 g of p-propylphenol and 32 g of 2,3-difluoro-4-pentyloxybiphenyl-4'-carboxylic acid (preparation of 4-pentyloxy-2,3-difluorobiphenyl-4'-carboxylic acid: pentyloxy-2,3-difluorobenzene is metalated with an equimolar amount of butyllithium and TMEDA under the customary conditions at $-70°$ C. in THF, and the reaction mixture is then stirred at $-70°$ C. for 4 hours and reacted with an equimolar amount of chlorotriisopropyl orthotitanate at the same temperature. The reaction mixture is allowed to warm slowly to $-30+$ C., an equimolar amount of ethyl cyclohexanone-4-carboxylate is then added and the mixture is stirred for 12 hours while warming slowly to room temperature. The reaction mixture is hydrolysed with ice-cold dilute hydrochloric acid, stirred briefly and filtered over celite. The filtrate is extracted with MTB ether and the organic phase is dried and evaporated. The residue is taken up in ethanol, a little hydrochloric acid is added and the mixture is boiled under reflux for 12 hours. After addition of water, the product is isolated in the customary manner and heated at the boiling point together with twice the molar amount of DDQ in toluene. The mixture is then worked up in the customary manner and the ester is hydrolysed with a small excess of ethanolic KOH at room temperature. The acid is purified by crystallization.) are initially introduced into 250 ml of methylene chloride together with a catalytic amount of DMAP, and a solution of 0.1 mol of DCC in methylene chloride is added dropwise at 0° C. The reaction mixture is stirred at room temperature for 12 hours, the dicyclohexylurea which has precipitated is then filtered off with suction and the organic phase is worked up in the customary manner. p-Propylphenyl 4-pentyloxy-2,3-difluorobiphenyl-4'-carboxylate is obtained.

The following compounds are prepared analogously:

p-hexylphenyl 4-pentyloxy-2,3-difluorobiphenyl-4'-carboxylate p-hexylphenyl 4-heptyloxy-2,3-difluorobiphenyl-4'-carboxylate p-hexylphenyl 4-octyloxy-2,3-difluorobiphenyl-4'-carboxylate p-hexylphenyl 4-nonyloxy-2,3-difluorobiphenyl-4'-carboxylate p-heptylphenyl 4-octyloxy-2,3-difluorobiphenyl-4'-ylcarboxylate p-octylphenyl 4-octyloxy-2,3-difluorobiphenyl-4'-ylcarboxylate, $C_1$ 58.6° $C_2$ 63.6° $S_C$ 121° $S_A$ 139.1° N 144.5° I p-nonylphenyl 4-octyloxy-2,3-difluorobiphenyl-4'-ylcarboxylate p-hexyloxyphenyl 4-octyloxy-2,3-difluorobiphenyl-4'-ylcarboxylate p-heptyloxyphenyl 4-octyloxy-2,3-difluorobiphenyl-4'-ylcarboxylate p-octyloxyphenyl 4-octyloxy-2,3-difluorobiphenyl-4'-ylcarboxylate, C 83.8° $S_C$ 151.7° $S_A$ 154.9° N 165.4° I 4-octyl-2-fluorophenyl 4-octyloxy-2,3-difluorobiphenyl-4'-ylcarboxylate, C56.7° $S_C$ 103° N 141.6° I 4-octyl-3-fluorophenyl 4-octyloxy-2,3-difluorobiphenyl-4'-ylcarboxylate, C 45.2° $S_C$ 84.3° N 120.7° I 4-hepthyl-3-fluorophenyl 4-octyloxy-2,3-difluorobiphenyl-4'-ylcarboxylate, C 44.7° $S_C$ (41°) $S_A$ 146° I 4-octyloxy-3-fluorophenyl 4-octyloxy-2,3-difluorobiphenyl-4'-ylcarboxylate, C 83.6° $S_C$ 116° $S_A$ 162.9° I

Example 29

39 g of 1-(4-ethoxy-2,3-difluorophenyl)-4-(4-trans-propyl-cyclohexylethyl)cyclohex-1-ene (preparation: 131 ml of a 1.6N solution of butyllithium (BuLi) in n-hexane are added dropwise to a solution of 31.6 g of ethoxy-2,3-difluorobenzene and 23.2 g of tetramethylethylenediamine (TMEDA) in 400 ml of tetrahydrofuran (THF) at $-70°$ C., with exclusion of moisture and under a nitrogen atmosphere. The mixture is then stirred at $-70°$ C. for 4 hours and 50 g of 4-(trans-4-n-propylcyclohexylethyl)-cyclohexanone in 100 ml of THF are subsequently slowly added. The reaction mixture is allowed to warm slowly to room temperature and is then hydrylysed with 1.5 l of a saturated ammonium chloride solution. The mixture is extracted with ether and the ether phase is washed several times with water, dried and evaporated. The residue is taken up in 700 ml of ethanol, 70 ml of concentrated HCl are added ad the mixture is boiled under reflux for 3 hours. 1.5 l of water are then added and the mixture is extracted with methyl tert.-butyl ether (MTB ether). The ether phase is washed until neutral, dried and evaporated and the residue is recrystallized.) are dissolved in 250 ml of THF and hydrogenated in the presence of 4 g of 5% Pd-C at 34° C. under a hydrogen pressure of 0.5 bar. The mixture is then filtered, the solution is evaporated and trans-4-(trans-4-n-propylcyclohexylethyl)-4-(ethoxy)-2,3-difluorophenyl)-cyclohexane is isolated chromatographically by crystallization, C 76° $S_B$ 79° N 186° I.

The following compounds are prepared anatogrously:

trans-4-(trans-4-ethylcyclohexylethyl)-4-ethoxy-2,3-difluorophenyl)-cyclohexane trans-4-(trans-4-butylcyclohexylethyl)-4-ethoxy-2,3-difluorophenyl)-cyclohexane trans-4-(trans-4-pentylcyclohexylethyl)-(4-ethoxy-2,3-difluorophenyl)-cyclohexane trans-4-(trans-4-hexylcyclohexylethyl)-(4-ethoxy-2,3-difluorophenyl)-cyclohexane trans-4-(trans-4-heptylcyclohexylethyl)-4-ethoxy-2,3-difluorophenyl)-cyclohexane trans-4-(trans-4-octylcyclohexylethyl)-4-ethoxy-2,3-difluorophenyl)-cyclohexane grans-4-(trans-4-ethylcyclohexylethyl)-4-octyloxy-2,3-difluorophenyl)-cyclohexane trans-4-(trans-4-butylcyclohexylethyl)-(4-octyloxy-2,3-difluorophenyl)-cyclohexane trans-4-(trans-4-pentylcyclohexylethyl)-(4-octyloxy-2,3-difluorophenyl)-cyclohexane trans-4-(trans-4-hexylcyclohexylethyl)-(4-octyloxy-2,3-difluorophenyl)-cyclohexane trans-4-(trans-4-heptylcyclohexylethyl)-(4-octyloxy-2,3-difluorophenyl)-cyclohexane trans-4-(trans-4-propylcyclohexylethyl)-4-octyloxy-2,3-difluorophenyl)-cyclohexane trans-4-(trans-4-octylcyclohexylethyl)-(4-octyloxy-2,3-difluorophenyl)-cyclohexane

Example 30

0.1 mol of 2,3-difluoro-4-nonyloxybenzamidine hydrochloride (prepared from 2,3-difluoro-4-nonyloxybenzoyl chloride by conversion into the amide, dehydration thereof to give the nitrile, reaction of the nitrile with ethanol and hydrogen chloride gas and subsequent reaction of the imido ester with ammonia), 0.1 mol of nonylmalonodialdehyde tetramethylacetal and 50 ml of DMF are heated at 150° for 12 hours. The reaction mixture is then taken up in methylene chloride, washed until neutral with sodium bicarbonate solution and water and dried and the solvent is distilled off. 2-(2,3-Difluoro-4-nonyloxyphenyl)-5-nonylpyrimidine is obtained as the residue and is recrystallized from ethanol, C 42° $S_C$ 54° I.

The following compounds are prepared anatogously:
2-(2,3-difluoro-4-octyloxyphenyl)-5-nonylpyrimidine
2-(2,3-difluoro-4-heptyloxyphenyl)-5-nonylpyrimidine
2-(2,3-difluoro-4-hexyloxyphenyl)-5-nonylpyrimidine
2-(2,3-difluoro-4-pentyloxyphenyl)-5-nonylpyrimidine
2-(2,3-difluoro-4-butoxyphenyl)-5-nonylpyrimidine
2-(2,3-difluoro-4-propoxyphenyl)-5-nonylpyrimidine
2-(2,3-difluoro-4-ethoxyphenyl)-5-nonylpyrimidine
2-(2,3-difluoro-4-ethylphenyl)-5-nonylpyrimidine
2-(2,3-difluoro-4-propylphenyl)-5-nonylpyrimidine
2-(2,3-difluoro-4-butylphenyl)-5-nonylpyrimidine
2-(2,3-difluoro-4-pentylphenyl)-5nonylpyrimidine
2-(2,3-difluoro-4-hexylphenyl)-5-nonylpyrimidine
2-(2,3-difluoro-4-heptylphenyl)-5-nonylpyrimidine
2-(2,3-difluoro-4-octylphenyl)-5-nonylpyrimidine
2-(2',3'-difluoro-4'-ethylbiphenyl-4-yl)-5-heptylpyrimidine
2-(2',3'-difluoro-4'-propylbiphenyl-4-yl)-5-heptylpyrimidine
2-(2',3'-difluoro-4'-butylbiphenyl-4-yl)-5-heptylpyrimidine
2-(2',3'-difluoro-4'-pentylbiphenyl-4-yl)-5-heptylpyrimidine
2-(2',3'-difluoro-4'-hexylbiphenyl-4-yl)-5-heptylpyrimidine
2-(2',3'-difluoro-4'-heptylbiphenyl-4-yl)-5-heptylpyrimidine
2-(2',3'-difluoro-4'-octylbiphenyl-4-yl)-5-heptylpyrimidine, C64° $S_C$ 90° N 188° I.

Example 31

2,3-Difluoro-4-(5-butylpyrimidin-2-yl)-4'-propylbiphenyl is obtained by reaction of 2,3-difluoro-4'-propyl-biphenyl-4-carbamidine hydrochloride (the biphenylcarboxylic acid required for this is obtained analogously to Example 28) with butylmalonodialdehyde tetramethylacetal in DMF, after customary working up.

Example 32

A solution of 0.1 mol of n-Buli in hexane is added dropwise to a solution of 0.1 mol of 2,3-difluorononyloxybenzene and 0.1 mol of TMEDA in 200 ml of THF at −60° to −70° C. in the course of half an hour, while stirring. The mixture is stirred at this temperature for a further 2 hours and a solution of 0.05 mol of ZnBr$_2$ (anhydrous) in 100 ml of THF is then added dropwise at the same temperature. After a further hour, a solution of 0.1 mol of 2-bromo-5-methylpyridine and 2 mol % (0.002 mol) of bis-triphenylphosphinenickel (II) chloride, dissolved in 50 ml of THF, is slowly added and the mixture is subsequently stirred for a further 16 hours, during which the temperature is allowed to reach room temperature slowly. Water is added and the mixture is worked up by extraction. The crude product is purified by recrystallization and chromatography. 2-(2,3-Difluoro-4-nonyloxyphenyl)-5-methylpyridine is obtained.

The following compounds are prepared analogously:
2-(2,3-difluoro-4-octyloxybiphenyl)-5-methylpyridine
2-(2,3-difluoro-4-octyloxybiphenyl)-5-ethylpyridine
2-(2,3-difluoro-4-octyloxybiphenyl)-5- propylpyridine
2-(2,3-difluoro-4-octyloxybiphenyl)-5- butylpyridine
2-(2,3-difluoro-4-octyloxybiphenyl)-5- pentylpyridine
2-(2,3-difluoro-4-octyloxybiphenyl)-5- hexylpyridine
2-(2,3-difluoro-4-octyloxybiphenyl)-5- heptylpyridine
2-(2,3-difluoro-4-octyloxybiphenyl)-5- octylpyridine $S_C$ 26° N 38.5° I

Example 33

0.1 mol of DCC, dissolved in methylene chloride, is added to a mixture of 0.1 mol of 4'-heptyloxy-2,3-difluorobiphenylcarboxylic acid (preparation: 0.1 mol of 2,3-difluoro-4'-heptyloxybiphenyl and 0.1 mol of TMEDA are dissolved in 200 ml of THF and the solution is cooled to −78° C. and reacted with 0.105 mol of a 1.6 N solution of Buli in hexane at this temperature. The reaction mixture is stirred at −78° C. for 3 hours and is then poured all at once onto 200 g of crushed dry ice. Customary working up gives 4'-heptyloxy-2,3-difluoro-biphenyl-4-carboxylic acid), 0.1 mol of optically active 2-cyano-2-methylhexan-1-ol (which can be prepared from optically active ethyl 2-methyl-2-butyl-cyanoacetate by reduction with LiBH$_4$) and a catalytic amount of 4-N,N'-dimethylaminopyridine (DMAP) in 200 ml of methylene chloride at 0° C. The mixture is then stirred at room temperature for 12 hours. It is worked up in the customary manner and the product is purified by crystallization. Optically active 2-cyano-2-methylhexyl 4'-heptyloxy-2,3-difluorobiphenyl-4-carboxylate is obtained.

Example 34

0.17 mol of diethyl azodicarboxylate (DEAD), dissolved in THF, is added to a solution of 0.15 mol of 4'-heptyloxy-2,3-difluorobiphenyl-4-ol, 0.17 mol of L(−)-ethyl lactate and 0.15 mol of triphenylphosphine in 400 ml of THF. During this addition, the reaction temperature should not exceed 50° C. The mixture is stirred at 50° C. for 1 hour and then at room temperature overnight. The solvent is then distilled off, the residue is dissolved in hot toluene and the solution is subsequently allowed to cool slowly. The triphenylphosphine oxide which has precipitated is filtered off with suction, the filtrate is concentrated and the residue is purified by chromatography. Ethyl 2-[4-(p-heptyloxyphenyl)-2,3-difluorophenoxyl]-propionate is obtained.

Example 35

A solution of 0.1 mol of DCC in methylene chloride is added to a mixture of 0.1 mol of 4'-heptyloxy-2,3-difluorobiphenyl-4-ol, 0.1 mol of optically active 2-chloro-3-methylbutyric acid (prepared from valine) and a catalytic amount of DMAP in 250 ml of methylene chloride at 0° C. The mixture is then stirred at room temperature for 12 hours, the precipitate is subsequently filtered off with suction and the filtrate is worked up in the customary manner to give 4-(p-heptyloxyphenyl)-2,3-difluorophenyl 2-chloro-3-methylbutyrate.

mann rearrangement), 0.1 mol of 0.1 mol of 4-propylbenzaldehyde, 0.01 mol of p-toluenesulfonic acid and 200 ml of toluene is heated at the boiling point for 2 hours using a water separator. Customary working up gives (4-octyloxy-2,3-difluorophenyl)-4-propylbenzylideneamine.

The following compounds are prepared analogously:
(4-octyloxy-2,3-difluorophenyl)-4-ethylbenzylideneamine
(4-octyloxy-2,3-difluorophenyl)-4-butylbenzylideneamine
(4-octyloxy-2,3-difluorophenyl)-4-pentylbenzylideneamine
(4-octyloxy-2,3-difluorophenyl)-4-hexylbenzylideneamine
(4-octyloxy-2,3-difluorophenyl)-4-heptylbenzylideneamine
(4-octyloxy-2,3-difluorophenyl)-4-octylbenzylideneamine
(4-pentyloxy-2,3-difluorophenyl)-4-ethylbenzylideneamine
(4-pentyloxy-2,3-difluorophenyl)-4-propylbenzylideneamine
(4-pentyloxy-2,3-difluorophenyl)-4-butylbenzylideneamine
(4-pentyloxy-2,3-difluorophenyl)-4-pentylbenzylideneamine
(4-pentyloxy-2,3-difluorophenyl)-4-hexylbenzylideneamine
(4-pentyloxy-2,3-difluorophenyl)-4-heptylbenzylideneamine
(4-pentyloxy-2,3-difluorophenyl)-4-octylbenzylideneamine

Example 41

66 ml of a 1.6N solution of butyllithium in n-hexane are added dropwise to a solution of 0.1 mol of 2,3-difluorophenetole and 0.1 mol of TMEDA in 200 ml of THF at −70° C. After stirring for 4 hours at −70° C. 0.1 mol of 4-acetyl-4'-propylbiphenyle in 50 ml of THF are added. After customary working up the product and 2 g of p-toluenesulfonic acid are dissolved in 200 ml of toluene and the mixtung is heated under reflux for 0.5 hours. Working up gives 1-(4-ethoxy-2,3-difluorphenyl)-1-(4'-propylbiphenyl-4-yl)-ethene.

0.065 mol of bromine are added to a stirred solution of 0.065 mol of this ethen derivative in a mixture of 100 ml of dichloromethane and 50 ml of acetonitrile. After addition of 10 g of triethylamine and customary working up the crude product is dissolved in 50 ml of THF. 0.13 mol of lithium diisopropylamide in 120 ml of THF are added dropwise to this solution at −50° C. Customary working up gives 1-(4-Ethoxy-2,3-difluorophenyl)-2-(4'-propylbiphenyl-4-yl)-ethine.

0.031 mol of this ethine-derivative and 3 g of Pd-C (5%) are suspended in 100 ml of THF and hydrogenated at room-temperature under a hydrogen pressure of 1 bar. Customary working up gives 1-(4-ethoxy-2,3-difluorophenyl)-2-(4'-propylbiphenyl-4-yl)-ethane.

The following compounds are prepared analogously:
1-(4-ethoxy-2,3-difluorophenyl)-2-(4'-ethylbiphenyl-4-yl)-ethane
1-(4-ethoxy-2,3-difluorophenyl)-2-(4'-butylbiphenyl-4-yl)-ethane
1-(4-ethoxy-2,3-difluorophenyl)-2-(4'-pentylbiphenyl-4-yl)-ethane
1-(4-ethoxy-2,3-difluorophenyl)-2-(4'-hexylbiphenyl-4-yl)-ethane
1-(4-ethoxy-2,3-difluorophenyl)-2-(4'-heptylbiphenyl-4-yl)-ethane
1-(4-ethoxy-2,3-difluorophenyl)-2-(4'-octylbiphenyl-4-yl)-ethane
1-(4-propyl-2,3-difluorophenyl)-2-(4'-ethylbiphenyl-4-yl)-ethane
1-(4-propyl-2,3-difluorophenyl)-2-(4'-propylbiphenyl-4-yl)-ethane
1-(4-propyl-2,3-difluorophenyl)-2-(4'-butylbiphenyl-4-yl)-ethane
1-(4-propyl-2,3-difluorophenyl)-2-(4'-pentylbiphenyl-4-yl)-ethane
1-(4-propyl-2,3-difluorophenyl)-2-(4'-hexylbiphenyl-4-yl)-ethane
1-(4-propyl-2,3-difluorophenyl)-2-(4'-heptylbiphenyl-4-yl)-ethane
1-(4-propyl-2,3-difluorophenyl)-2-(4'-octylbiphenyl-4-yl)-ethane

Example 42

A.

4-(Trans-4-Pentylcyclohexylmethoxy)-2,3-difluorophenylboronic acid

A solution of n-butyllithium in hexane (60 ml, 1.6 mol/l) is added to a mixture of 3-(trans-4-pentylcyclohexylmethoxy)-1,2-difluorobenzene (obtained from 4-trans-pentylcyclohexylmethylbromide and 2,3-difluorophenole as example 4), 200 ml of THF and 0.1 mol of TMEDA at −70° C. is stirred for 4 hours.

Then a solution of 0.11 mol of trimethylborate in 40 ml THF is added. After warming up to room temperature a solution of hydrochloric acid (300 ml, 10%) is added. Customary working up gives the product as a solid.

B.

4'-(trans-4-Pentylclycohexylmethoxy)-2',3',4-trifluorobiphenyle 0.05 mol of the boronic acid (42 A) in 100 ml ethanole are coupled with 0.05 ml of p-fluoroidobenzene and with tetrakis (triphenylphosphin)palladium (0) as catalysator in a mixture of toluene (50 ml) and a laqueous solution of sodium carbonate (50 ml, 2 mol/l) (V. Snieckus et al. Tetrahedron Letters 28, No. 43, 5093–5096, 1987).

The product is obtained as a solid K 85° N 102° I.

The following compounds are prepared analogously:
4'-(trans-4-ethylcyclohexylmethoxy)-2',3',4-trifluorobiphenyle
4'-(trans-4-propylcyclohexylmethoxy)-2',3',4-trifluorobiphenyle
4'-(trans-4-butylcyclohexylmethoxy)-2',3',4-trifluorobiphenyle
4'-(trans-4-hexylcyclohexylmethoxy)-2',3',4-trifluorobiphenyle
4'-(trans-4-heptylcyclohexylmethoxy)-2',3',4-trifluorobiphenyle
4'-(trans-4-octylcyclohexylmethoxy)-2',3',4-trifluorobiphenyle With p-iodo-(trifluoromethoxy)-benzene as starting material are obtained:
4'-(trans-4-ethylcyclohexylmethoxy)-2',3'-difluoro-4-trifluoromethoxybiphenyle
4'-(trans-4-propylcyclohexylmethoxy)-2',3'-difluoro-4-trifluoromethoxybiphenyle
4'-(trans-4-butylcyclohexylmethoxy)-2',3'-difluoro-4-trifluoromethoxybiphenyle

Example 36

0.0055 mol of 4-octylbicyclo[2,2,2]octylcarboxyl chloride is added to a mixture of 0.0055 mol of 4'-octyloxy-2',3'-difluorobiphenyl-4-ol (prepared by hydrogenolytic cleavage of 4'-octyloxy-2',3'-difluoro-4-benzyloxybiphenyl, which is obtained by coupling of 4-octyloxy- 2,3-difluorophenyl diisopropyloxytitanate to p-benzyloxybromobenzene with tetrakis(triphenylphosphine)palladium (0) as the catalyst), 20 ml of methylene chloride and 1 ml of triethylamine. After the mixture has been stirred at 20° for 24 hours, customary working up gives 4'-octyloxy-2',3'-difluorobiphenyl-4-yl 4-octylbicyclo-[2,2,2]octylcarboxylate, C 57.1° $S_C$ 128.5° $S_A$ 156° N 177.5.

The following compounds are prepared analogously:
4'-octyloxy-2',3'-difluorobiphenyl-4-yl trans -4-heptylcyclohexlcarboxylate, C 53° $S_C$ 132.8° $S_A$ 144.4° N 162° I
4'-octyloxy-2',3'-difluoro-4-acetyloxybiphenyl
4'-octyloxy-2',3'-difluoro-4-propionyloxybiphenyl
4'-octyloxy-2',3'-difluoro-4-butyryloxybiphenyl
4'-octyloxy-2',3'-difluoro-4-pentanoyloxybiphenyl
4'-octyloxy-2',3'-difluoro-4-hexanoyloxybiphenyl
4'-octyloxy-2',3'-difluoro-4-heptanoyloxybiphenyl, C 62.9° I
4'-octyloxy-2',3'-difluoro-4-octanoyloxybiphenyl, C 54.9° $S_C$ 63.0° N 66.5° I
4'-octyloxy-2',3'-difluoro-4-nonanoyloxybiphenyl, C 58° $S_C$ 63.1° N 63.5° I
4'-octyloxy-2',3'-difluoro-4-(4-methylhexanoyloxy)-biphenyl C 38° $S_C$ (32.5°) N (35.5°) I
4'-octyloxy-2',3'-difluoro-4-decanoyloxy, C 51.8° $S_C$ 71° I

Example 37

A mixture of 0.2 mol of 4-(4-trans-pentylcyclohexyl)-1-(4- octyloxy-2,3-difluorophenyl)-cyclohex-1-ene (prepared from 4-octyloxy-2,3-difluorophenyllithium and 4-trans-4-pentylcyclohexyl)-cyclohexanone and subsequent dehydration with p-toluenesulfonic acid), 400 ml of toluene and 0.4 mol of DDQ is heated at the boiling point for 2 hours. After cooling, 4'-(trans-4-pentylcyclohexyl)-4-octyloxy-2,3-difluorobiphenyl is obtained, C 53° $S_C$ 58 $S_A$ 127° N.

The following compounds are prepared analogously:
4'-(trans-4-pentylcyclohexyl)-4-heptyloxy-2,3-difluorobiphenyl
4'-(trans-4-pentylcyclohexyl)-4-hexyloxy-2,3-difluorobiphenyl
4'-(trans-4-pentylcyclohexyl)-4-pentyloxy-2,3-difluorobiphenyl
4'-(trans-4-pentylcyclohexyl)-4-butyoxy-2,3-difluorobiphenyl
4'-(trans-4-pentylcyclohexyl)-4-propoxy-2,3-difluorobiphenyl
4'-(trans-4-pentylcyclohexyl)-4-ethoxy-2,3-difluorobiphenyl
4'-(trans-4-pentylcyclohexyl)-4-ethyl-2,3-difluorobiphenyl
4'-(trans-4-pentylcyclohexyl)-4-propyl-2,3-difluorobiphenyl
4'-(trans-4-pentylcyclohexyl)-4-butyl-2,3-difluorobiphenyl
4'-(trans-4-pentylcyclohexyl)-4-pentyl-2,3-difluorobiphenyl
4'-(trans-4-pentylcyclohexyl)-4-hexyl-2,3-difluorobiphenyl
4'-(trans-4-pentylcyclohexyl)-4-heptyl-2,3-difluorobiphenyl
4'-(trans-4-pentylcyclohexyl)-4-octyl-2,3-difluorobiphenyl

Example 38

A solution of 0.2 mol of n-butyllithium in 65 ml of hexane is added to a mixture of 0.1 mol of 1,2-difluorobenzene, 0.2 mol of potassium tert.-butylate and 100 ml of tetrahydrofuran at −100° C. After the mixture has been stirred for 10 minutes, a mixture of 0.2 mol of 4-propylcyclohexanone and 20 ml of tetrahydrofuran is added at −90° C. After the mixture has been stirred at −40° C. for 2 hours, it is warmed to room temperature and 30 ml of 2 normal hydrochloric acid solution are added. Heating for 2 hours and customary working up give 1,4-bis-(4-propylcyclohex-1-enyl)-2,3-difluorobenzene, C 59° N 120° I.

The following compounds are prepared analogously:
1,4-bis-(4-ethylcyclohex-1-enyl)-2,3-difluorobenzene
1,4-bis-(4-butylcyclohex-1-enyl)-2,3-difluorobenzene
1,4-bis-(4-pentylcyclohex-1-enyl)-2,3-difluorobenzene
1,4-bis-(4-hexylcyclohex-1-enyl)-2,3-difluorobenzene
1,4-bis-(4-heptylcyclohex-1-enyl)-2,3-difluorobenzene
1,4-bis-(4-octylcyclohex-1-enyl)-2,3-difluorobenzene

Example 39

A mixture of 0.1 mol of (trans-4-pentylcyclohexyl)-acetyl chloride and 20 ml of toluene is added to a mixture of 0.1 mol of 4-octyloxy-2,3-difluorophenylboric acid (prepared from 4-octyloxy-2,3-difluorophenyllithium and triisopropyl borate and subsequent hydrolysis with dilute hydrochloric acid), 0.2 mol of sodium carbonate, 0.01 mol of tetrakis-(triphenylphosphine) palladium (0) and 150 ml of toluene at 0° C. After the mixture has been stirred at room temperature for 2 hours, customary working up gives 1-(4-octyloxy-2,3-difluorophenyl)-2-trans-4-pentylcyclohexyl)-ethan-1-one, C 59° $S_A$ (55°) I.

The following compounds are prepared analogously:
1-(1-octyloxy-2,3-difluorophenyl)2-(trans-4-ethylcyclohexyl)-ethan-1-one
1-(1-octyloxy-2,3-difluorophenyl)2-(trans-4-propylcyclohexyl)-ethan-1-one
1-(1-octyloxy-2,3-difluorophenyl)2-(trans-4-butylcyclohexyl)-ethan-1-one
1-(1-octyloxy-2,3-difluorophenyl)2-(trans-4-hexylcyclohexyl)-ethan-1-one
1-(1-octyloxy-2,3-difluorophenyl)2-(trans-4-heptylcyclohexyl)-ethan-1-one
1-(1-octyloxy-2,3-difluorophenyl)2-(trans-4-octylcyclohexyl)-ethan-1-one
1-(1-pentyloxy-2,3-difluorophenyl)2-(trans-4-ethylcyclohexyl)-ethan-1-one
1-(1-pentyloxy-2,3-difluorophenyl)2-(trans-4-propylcyclohexyl)-ethan-1-one
1-(1-pentyloxy-2,3-difluorophenyl)2-(trans-4-butylcyclohexyl)-ethan-1-one
1-(1-pentyloxy-2,3-difluorophenyl)2-(trans-4-hexylcyclohexyl)-ethan-1-one
1-(1-pentyloxy-2,3-difluorophenyl)2-(trans-4-heptylcyclohexyl)-ethan-1-one
1-(1-pentyloxy-2,3-difluorophenyl)2-(trans-4-octylcyclohexyl)-ethan-1-1-one

Example 40

A mixture of 0.1 mol of 4-octyloxy-2,3-difluoroaniline (prepared from the corresponding amide by a Hoff- 4'-(trans-4-pentylcyclohexylmethoxy)-2',3'-difluoro-4-trifluoromethoxybiphenyle, K 52° $S_A$ 76° N 108° I 4'-(trans-4-hexylcyclohexylmethoxy)-2',3'-difluoro-4-trifluoromethoxybiphenyle 4'-(trans-4-heptylcyclohexylmethoxy)-2',3'-difluoro-4-trifluoromethoxybiphenyle 4'-(trans-4-octylcyclohexylmethoxy)-2',3'-difluoro-4-trifluoromethoxybiphenyle With p-bromo-(trifluoromethyl)-benzene as stating material one obtained:

4'-(trans-4-ethylcyclohexylmethoxy)-2',3'-difluoro-4-trifluoromethylbiphenyle

4'-(trans-4-propylcyclohexylmethoxy)-2',3'-difluoro-4-trifluoromethylbiphenyle

4'-(trans-4-butylcyclohexylmethoxy)-2',3'-difluoro-4-trifluoromethylbiphenyle

4'-(trans-4-pentylcyclohexylmethoxy)-2',3'-difluoro-4-trifluoromethylbiphenyl, K 72° N 90° I 4'-(trans-4-hexylcyclohexylmethoxy)-2',3'-difluoro-4-trifluoromethylbiphenyle 4'-(trans-4-heptylcyclohexylmethoxy)-2',3k'-difluoro-4-trifluoromethylbiphenyle 4'-(trans-4-octylcyclohexylmethoxy)-2',3'-difluoro-4-trifluoromethylbiphenyle

Example A

A liquid crystal medium consisting of
8% of 2-p-heptyloxyphenyl-5-octylpyrimidine,
10% of 2-p-octyloxyphenyl-5-octylpyrimidine,
14% of 2-p-nonyloxyphenyl-5-octylpyrimidine,
3% of 2-p-hexyloxyphenyl-5-nonylpyrimidine,
23% of 2-p-nonyloxyphenyl-5-nonylpyrimidine,
7% of 2-(2,3-difluoro-4-nonyloxyphenyl)-5-octylpyrimidine,
9% of 2-(2,3-difluoro-4-nonyloxyphenyl)-5-nonylpyrimidine,
8% of 2-(p-pentyloxyphenyl)-5-(p-octylphenyl)-1,3,4-thiadiazole,
8% of 2-(p-heptyloxyphenyl)-5-(p-octylphenyl)-1,3,4-thiadiazole and
10% of optically active 4'-octyloxybiphenyl-4-yl 2-cyano-2-methylhexanecarboxylate
shows $S_c^*$ 61 $S_A$ 66 Ch 72 I and a spontaneous polarization of 18 nC/cm² at room temperature.

Example B

A liquid crystal medium consisting of
4% of 2-p-octyloxyphenyl-5-heptylpyrimidine,
4% of 2-p-nonyloxyphenyl-5-heptylpyrimidine,
7% of 2-p-hexyloxyphenyl-5-nonylpyrimidine,
12% of 2-p-heptyloxyphenyl-5-nonylpyrimidine,
25% of 2-p-nonyloxyphenyl-5-nonylpyrimidine,
8% of 2-(2,3-difluoro-4-nonyloxyphenyl)-5-nonylpyrimidine,
8% of 2-(2,3-difluoro-4-octyloxybiphenyl-4'-yl)-5-heptylpyrimidine,
8% of r-1-cyano-cis-4-(4'-octyloxybiphenyl-4-yl)-1-octylcyclohexane,
7% of 2-(p-heptyloxyphenyl)-5-(p-pentylphenyl)-1,3,4-thiadiazole,
7% of 2-(p-octyloxyphenyl)-5-(p-heptylphenyl)-1,3,4-thiadiazole and
10% of chiral ethyl 2-[p-(5-nonylpyrimidin-2-yl)-phenoxy]-propionate
shows $S_c^*$ 58 $S_A$ 64 Ch 75 I and a spontaneous polarization of 10 nC/cm² at room temperature.

Example C

A liquid crystal medium consisting of
12.5% of 4-heptyloxy-2,3-difluorophenyl 4'-octyloxybiphenyl-4-ylcarboxylate
14.2% of 4-heptyloxy-2,3-difluuorophenyl 4-octyloxybenzoate
12.5% of 4-hepthyl-2-fluorophenyl 4'-heptyloxybiphenyl-4-ylcarboxylate
12.5% of 4-heptyl-2-fluorophenyl 4'-heptyloxy-2'-fluorobiphenyl-4-ylcarboxylate
14.2% of 4-octyloxy-3-fluorophenyl 4-octyloxybenzoate
12.34% of 4-pentyl-2-fluorophenyl 4-octyloxybenzoate
14.24% of 4-octyloxy-3-fluorophenyl 4-heptyloxybenzoate
5.04% of chiral 4-(2-methylbutyl)-phenyl 4'-octylbiphenyl-4-ylcarboxylate and
2.48% of chiral 1-cyano-2-methylpropyl 4'-octyloxybiphenyl-4-ylcarboxylate
shows $S_C^*$ 66.4° $S_A$ 73° Ch 97.2° I and a spontaneous polarization of 9 nC/cm² at 30° C.

Example D

A liquid crystal medium consisting of
16.87% of 4-heptyl-2-fluorophenyl 4'-heptyloxybiphenyl-4-ylcarboxylate
16.87% of 4-heptyl-2-fluorophenyl 4'-heptyloxy-2'-fluorobiphenyl-4-ylcarboxylate
16.87% of 4-octyl-2-fluorophenyl 4'-octyloxy-2',3'-difluorobiphenyl-4-ylcarboxylate
14% of 4-octyloxy-3-fluorophenyl 4-octyloxybenzoate
14% of 4-hexyloxy-3-fluorophenyl 4-octyloxybenzoate
10% of 4-octyloxy-2-fluorophenyl 4-pentylbenzoate
9% of 4-heptyl-3-fluorophenyl 4'-octyloxy-2'3'-difluorobiphenyl-4-ylcaraobylate and
2.4% of chiral 1-cyano-2-methylpropyl 4'-octyloxybiphenyl-4-ylcarboxylate
shows $S_C^*$ 71.8° $S_A$ 81° Ch 103.8 I and a high spontaneous polarization.

Example E

A liquid crystal medium is formulated containing the following compounds:
13.5% 4'-(trans-4-pentylcyclohexyl)-4-cyanobiphenyle,
21.6% 4-(trans-4propylcyclohexyl)-benzonitrile,
32.4% 4-(trans-4-pentylcyclohexyl)-benzonitrile,
22.5% 4-(trans-4-heptylcyclohexyl)-benzonitrile and
10.0% 4-ethoxy-2,3-difluoro-4'-trifluoromethoxybiphenyle.

This medium exhibits the following physical properties:

clearing point 58.3° C., $\eta$ (20° C.) 26.0 mm²/s
$\Delta\epsilon$ +13.1, $\Delta n$ 0.1358

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A 2,3-difluorobenzene derivative of the formula

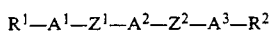

wherein

R[1] and R[2] are each independently $C_{1-15}$-alkyl; $C_{1-15}$-alkyl wherein at least one $CH_2$ group is replaced by —O—, —S—, —CO—, —O—CO—, —S—CO—, —O—COO—, —CO—S—, —CO—O— or —E—, two oxygen or sulfur atoms not being linked directly, E is $CR^3=CR^4$ R[3] and R[4] are each independently H, $C_{1-6}$-alkyl, F, Cl, Br, $CF_3$ or CN, Z[1] is —$CH_2CH_2$—, Z[2] is a single bond, A[1], A[2] and A[3] are each independently 1,4-phenylene; 1,4-phenylene substituted by one or more halogen, nitrile and/or methyl, with the proviso that at least the ring A[1] is 2,3-difluoro-1,4-phenylene.

2. A compound according to claim 1, wherein R[1] is $C_{1-12}$-alkyl or $C_{1-12}$-alkoxy.

3. A compound according to claim 1, of the formula

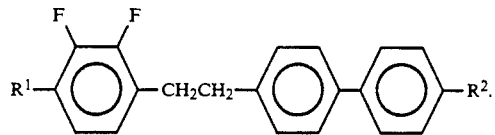

4. In a liquid crystal phase comprising at least two liquid crystal components, the improvement wherein at least one component is compound of claim 1.

5. In a liquid crystal phase comprising at least two liquid crystal components, the improvement wherein at least one component is a compound of claim 2.

6. In a liquid crystal phase comprising at least two liquid crystal components, the improvement wherein at least one component is a compound of claim 3.

7. In an electrooptical display element containing a liquid crystal dielectric, the improvement wherein the dielectric is a phase according to claim 4.

8. In an electrooptical display element containing a liquid crystal dielectric, the improvement wherein the dielectric is a phase according to claim 5.

9. In an electrooptical display element containing a liquid crystal dielectric, the improvement wherein the dielectric is a phase according to claim 6.

10. A compound according to claim 1 wherein R[1] is $C_{1-12}$-alkoxy.

11. A compound according to claim 3 wherein R[1] is $C_{1-12}$-alkoxy.

* * * * *